(12) United States Patent
Zarepisheh et al.

(10) Patent No.: US 12,083,359 B2
(45) Date of Patent: Sep. 10, 2024

(54) METHODS AND SYSTEMS FOR AUTOMATIC RADIOTHERAPY TREATMENT PLANNING

(71) Applicant: MEMORIAL SLOAN KETTERING CANCER CENTER, New York, NY (US)

(72) Inventors: Masoud Zarepisheh, New York, NY (US); Joseph O. Deasy, New York, NY (US); Linda Hong, New York, NY (US); Gig S. Mageras, New York, NY (US); Margie A. Hunt, New York, NY (US); James G. Mechalakos, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 907 days.

(21) Appl. No.: 16/978,397

(22) PCT Filed: Mar. 7, 2019

(86) PCT No.: PCT/US2019/021206
§ 371 (c)(1),
(2) Date: Sep. 4, 2020

(87) PCT Pub. No.: WO2019/173625
PCT Pub. Date: Sep. 12, 2019

(65) Prior Publication Data
US 2021/0252310 A1 Aug. 19, 2021

Related U.S. Application Data

(60) Provisional application No. 62/639,823, filed on Mar. 7, 2018.

(51) Int. Cl.
*A61N 5/10* (2006.01)

(52) U.S. Cl.
CPC .......... *A61N 5/1045* (2013.01); *A61N 5/1031* (2013.01); *A61N 5/1049* (2013.01)

(58) Field of Classification Search
CPC ............................................. A61N 5/103–1047
See application file for complete search history.

(56) References Cited

U.S. PATENT DOCUMENTS

2004/0001569 A1 1/2004 Luo
2008/0298550 A1\* 12/2008 Otto ..................... A61N 5/1047
378/65

(Continued)

OTHER PUBLICATIONS

Fu et al. "A Convex Optimization Approach to Radiation Treatment Planning with Dose Constraints." In: Cornell University Library/ Physics/ Medical Physics, Nov. 24, 2018.

(Continued)

*Primary Examiner* — Thaddeus B Cox
(74) *Attorney, Agent, or Firm* — Foley & Lardner LLP

(57) ABSTRACT

Systems and methods for improved radiation treatment planning can employ hierarchical constrained optimization with relaxed constraints also referred to herein after as expedited hierarchical constrained optimization (ECHO). The systems and methods described herein employ a combination of constrained optimization and a correction loop involving unconstrained optimization to enhance the speed and efficiency of the radiation treatment planning process and improve the accuracy and quality of resulting radiation treatment plans. The use of a hierarchical constrained optimization approach leads to less complex and faster to solve optimization problems. The correction loop allows for compensating for optimization error associated with the sequence of constrained optimizations by incorporating such error in an unconstrained optimization. Hard and soft dose volume constraints can be efficiently incorporated.

20 Claims, 10 Drawing Sheets

(56) References Cited

U.S. PATENT DOCUMENTS

| | | | |
|---|---|---|---|
| 2011/0081002 A1 | 4/2011 | Keall et al. | |
| 2011/0107270 A1 | 5/2011 | Wang et al. | |
| 2011/0255665 A1 | 10/2011 | Breedveld | |
| 2012/0203053 A1 | 8/2012 | Kilby et al. | |
| 2013/0072742 A1* | 3/2013 | Nord | A61N 5/1031 |
| | | | 600/1 |
| 2017/0036043 A1 | 2/2017 | Dilmanian et al. | |
| 2017/0177812 A1 | 6/2017 | Sjolund | |
| 2019/0030370 A1* | 1/2019 | Hibbard | A61N 5/1067 |
| 2019/0030372 A1 | 1/2019 | MacDonald et al. | |
| 2019/0255354 A1 | 8/2019 | Nordstrom et al. | |

OTHER PUBLICATIONS

International Search Report on PCT PCT/US2021/058066 Dtd Feb. 4, 2022.

Craft David et al: "An Approach for Practical Multiobjective IMRT Treatment Planning", International Journal of Radiation: Oncology Biology Physics, vol. 69, No. 5, Oct. 24, 2007 (Oct. 24, 2007), pp. 1600-1607.

Dan Nguyen et al: "A feasibility study for predicting optimal radiation therapy dose distributions of prostate cancer patients from patient anatomy using deep learning", arxiv.org, Cornell University Library, 201 Olin Library Cornell University Ithaca, NY 14853, Sep. 26, 2017 (Sep. 26, 2017), XP081037675.

Sebastiaan Breedveld et al: The equivalence of multi-criteria methods for radiotherapy plan optimization; Equivalence of multi-criteria methods11 , Physics in Medicine and Biology, Institute of Physics Publishing, Bristol GB, vol. 54, No. 23, Dec. 7, 2009 (Dec. 7, 2009), pp. 7199-7209.

International Search Report on PCT PCT/US2019/021206 dated Jul. 23, 2019 (4 pages).

* cited by examiner

METHODS AND SYSTEMS FOR AUTOMATIC RADIOTHERAPY TREATMENT PLANNING

RELATED APPLICATIONS

This application is a National Stage Application of PCT/US2019/021206, filed Mar. 7, 2019, which claims priority to U.S. Provisional Application No. 62/639,823, entitled "METHODS AND SYSTEMS FOR AUTOMATIC RADIOTHERAPY TREATMENT PLANNING" and filed on Mar. 7, 2018, the disclosure of each of which is incorporated herein by reference in its entirety.

FIELD OF THE DISCLOSURE

The present application relates generally to systems and methods for automatic radiotherapy treatment planning. Specifically, the present application relates to automatic radiotherapy treatment planning using expedited hierarchical constrained optimization (ECHO).

BACKGROUND

Radiotherapy is a localized cancer treatment using radiation to treat the tumor. The portion of a patient's body that is intended to receive radiation (e.g., identified by a doctor to receive radiation) is referred to as the planning target volume (PTV). The premise of radiotherapy is to deliver enough radiation to the PTV to damage the cancerous cells and avoid excess radiation to adjacent organs and anatomical regions referred to as adjacent organs at risk (OARs). Once PTV and OARs are identified for a patient using some imaging technique(s) (e.g., computed tomography (CT), magnetic resonance imaging (MRI), positron emission tomography (PET), or other imaging modality, or a combination thereof), the patient is immobilized on the couch of a radiation machine and a gantry equipped with a linear accelerator rotates around the patient to deliver radiation from different angles with various intensities and shapes.

The radiation beam used to damage cancerous cells can be shaped using a device that is called Multi Leaf Collimator (MLC) which is mounted on the head of the gantry. The MLC includes a set of metal leaves that move in-and-out and block parts of the radiation to modulate the beam and make the radiation more conformal to the PTV shape. There are different radiotherapy techniques including Intensity Modulated Radiation Therapy (IMRT) and Volumetric Modulated Arc Therapy (VMAT). In IMRT, the gantry stops at few angles (e.g., about 5 to 10 angles) and delivers the radiation by modulating the beams. In VMAT, the gantry delivers the radiation continuously while moving around the patient.

Radiotherapy treatment planning is very complex and patient specific problem. A treatment planner determines the radiation machine parameters such as beam intensities and beam shapes (MLC leaf positions) which are optimized based on the patient's specific geometry (e.g., tumor(s) shape(s), tumor(s) location(s), shape(s) and location(s) of OARs) and the physician's prescription dose. A patient can wait for weeks until a radiation therapy plan specific to the patient is ready.

SUMMARY

According to one aspect, a method of intensity modulated radiation therapy (IMRT) treatment planning can include accessing, by one or more processors, patient specific data of a patient. The patient specific data can include one or more parameters of an anatomical region of the patient, and the anatomical region can include a planning target volume (PTV) for which radiation to be applied and one or more anatomical sub-regions corresponding to normal tissues. The method can include the one or more processors determining, using the patient specific data, a first radiation beam profile by maximizing radiation to the PTV subject to a first set of constraints. The method can include the one or more processors determining, using the first radiation beam profile, a second radiation beam profile by minimizing one or more radiation dose based functions within the one or more anatomical sub-regions corresponding to the normal tissues subject to a second set of constraints. The method can include the one or more processors determining a third radiation beam profile by smoothing the second radiation beam profile subject to a third set of constraints. The method can include the one or more processors determining a radiation dose discrepancy between an optimization radiation dose vector associated with the third radiation profile and a simulated radiation dose vector determined based on the third radiation profile. The method can include the one or more processors determining, using the third radiation profile, a fourth radiation beam profile by reducing the determined radiation dose discrepancy.

According to one other aspect, a radiation treatment planning system for performing intensity modulated radiation therapy (IMRT) treatment planning can include one or more processors and a memory to store computer code instructions. The computer code instructions, when executed cause, the one or more processors to access patient specific data of a patient. The patient specific data can include one or more parameters of an anatomical region of the patient, and the anatomical region can include a planning target volume (PTV) for which radiation to be applied and one or more anatomical sub-regions corresponding to normal tissues. The one or more processors can determine, using the patient specific data, a first radiation beam profile by maximizing radiation to the PTV subject to a first set of constraints. The one or more processors can determine, using the first radiation beam profile, a second radiation beam profile by minimizing one or more radiation dose based functions within the one or more anatomical sub-regions corresponding to the normal tissues subject to a second set of constraints. The one or more processors can determine a third radiation beam profile by smoothing the second radiation beam profile subject to a third set of constraints. The one or more processors can determine a radiation dose discrepancy between an optimization radiation dose vector associated with the third radiation profile and a simulated radiation dose vector determined based on the third radiation profile. The one or more processors can determine, using the third radiation profile, a fourth radiation beam profile by reducing the determined radiation dose discrepancy.

According to yet one other aspect, a computer readable medium can include computer code instructions stored thereon. The computer code instructions when executed cause one or more processors to perform a method that includes accessing, by one or more processors, patient specific data of a patient. The patient specific data can include one or more parameters of an anatomical region of the patient, and the anatomical region can include a planning target volume (PTV) for which radiation to be applied and one or more anatomical sub-regions corresponding to normal tissues. The method can include the one or more processors determining, using the patient specific data, a first radiation beam profile by maximizing radiation to the PTV subject to a first set of constraints. The method can include the one or more processors determining, using the first radiation beam profile, a second radiation beam profile by minimizing one or more radiation dose based functions within the one or more anatomical sub-regions corresponding to the normal tissues subject to a second set of constraints. The method can include the one or more processors determining a third radiation beam profile by smoothing the second radiation beam profile subject to a third set of constraints. The method can include the one or more processors determining a radiation dose discrepancy between an optimization radiation dose vector associated with the third radiation profile and a simulated radiation dose vector determined based on the third radiation profile. The method can include the one or more processors determining, using the third radiation profile, a fourth radiation beam profile by reducing the determined radiation dose discrepancy.

According to one aspect, a method of volumetric modulated arc therapy (VMAT) treatment planning can include accessing, by one or more processors, patient specific data of a patient. The patient specific data can include one or more parameters of an anatomical region of the patient, and the anatomical region can include a planning target volume (PTV) for which radiation to be applied and one or more anatomical sub-regions corresponding to normal tissues. The method can include the one or more processors determining, using the patient specific data, a first set of beam apertures and a corresponding first set of radiation intensities subject to a first set of constraints. Each first beam aperture of the first set of beam apertures can be associated with a corresponding first radiation intensity of the first set of radiation intensities. The method can include the one or more processors determining, using the first set of beam apertures and the corresponding first set of radiation intensities, a second set of beam apertures and a corresponding second set of radiation intensities by minimizing one or more radiation dose based functions within the one or more anatomical sub-regions corresponding to the normal tissues subject to a second set of constraints. Each second beam aperture of the second set of beam apertures can be associated with a corresponding second radiation intensity of the second set of radiation intensities. The method can include the one or more processors determining a third set of beam apertures and a corresponding third set of radiation intensities by reducing at least one of a number of beam apertures or dissimilarities between adjacent apertures associated with the second set of beam apertures. The method can include the one or more processors identifying an arc-therapy radiation plan by computing a series of trajectories of a radiation source that traverse beam apertures of the third set of beam apertures. The method can include the one or more processors determining a radiation dose discrepancy between an optimization radiation dose vector associated with the third set of beam apertures and the corresponding third set of radiation intensities and a simulated radiation dose vector determined based on the arc-therapy radiation plan. The method can include the one or more processors determining, using the third set of beam apertures and the corresponding third set of radiation intensities, a fourth set of apertures and a corresponding fourth set of radiation intensities by reducing the determined radiation dose discrepancy.

According to one other aspect, a radiation treatment planning system for performing volumetric modulated arc therapy (VMAT) treatment planning can include one or more processors and a memory to store computer code instructions. The computer code instructions, when executed cause, the one or more processors to access patient specific data of a patient. The patient specific data can include one or more parameters of an anatomical region of the patient, and the anatomical region can include a planning target volume (PTV) for which radiation to be applied and one or more anatomical sub-regions corresponding to normal tissues. The one or more processors can determine, using the patient specific data, a first set of beam apertures and a corresponding first set of radiation intensities subject to a first set of constraints. Each first beam aperture of the first set of beam apertures can be associated with a corresponding first radiation intensity of the first set of radiation intensities. The one or more processors can determine, using the first set of beam apertures and the corresponding first set of radiation intensities, a second set of beam apertures and a corresponding second set of radiation intensities by minimizing one or more radiation dose based functions within the one or more anatomical sub-regions corresponding to the normal tissues subject to a second set of constraints. Each second beam aperture of the second set of beam apertures can be associated with a corresponding second radiation intensity of the second set of radiation intensities. The one or more processors can determine a third set of beam apertures and a corresponding third set of radiation intensities by reducing at least one of a number of beam apertures or dissimilarities between adjacent apertures associated with the second set of beam apertures. The one or more processors can identify an arc-therapy radiation plan by computing a series of trajectories of a radiation source that traverse beam apertures of the third set of beam apertures. The one or more processors can determine a radiation dose discrepancy between an optimization radiation dose vector associated with the third set of beam apertures and the corresponding third set of radiation intensities and a simulated radiation dose vector determined based on the arc-therapy radiation plan. The one or more processors can determine, using the third set of beam apertures and the corresponding third set of radiation intensities, a fourth set of apertures and a corresponding fourth set of radiation intensities by reducing the determined radiation dose discrepancy.

According to yet one other aspect, a computer readable medium can include computer code instructions stored thereon. The computer code instructions when executed cause one or more processors to perform a method that includes accessing, by one or more processors, patient specific data of a patient. The patient specific data can include one or more parameters of an anatomical region of the patient, and the anatomical region can include a planning target volume (PTV) for which radiation to be applied and one or more anatomical sub-regions corresponding to normal tissues. The method can include the one or more processors determining, using the patient specific data, a first set of beam apertures and a corresponding first set of radiation intensities subject to a first set of constraints. Each first beam aperture of the first set of beam apertures can be associated with a corresponding first radiation intensity of the first set of radiation intensities. The method can include the one or more processors determining, using the first set of beam apertures and the corresponding first set of radiation intensities, a second set of beam apertures and a corresponding second set of radiation intensities by minimizing one or more radiation dose based functions within the one or more anatomical sub-regions corresponding to the normal tissues subject to a second set of constraints. Each second beam aperture of the second set of beam apertures can be associated with a corresponding second radiation intensity of the second set of radiation intensities. The method can include the one or more processors determining a third set of beam apertures and a corresponding third set of radiation intensities by reducing at least one of a number of beam apertures or dissimilarities between adjacent apertures associated with the second set of beam apertures. The method can include the one or more processors identifying an arc-therapy radiation plan by computing a series of trajectories of a radiation source that traverse beam apertures of the third set of beam apertures. The method can include the one or more processors determining a radiation dose discrepancy between an optimization radiation dose vector associated with the third set of beam apertures and the corresponding third set of radiation intensities and a simulated radiation dose vector determined based on the arc-therapy radiation plan. The method can include the one or more processors determining, using the third set of beam apertures and the corresponding third set of radiation intensities, a fourth set of apertures and a corresponding fourth set of radiation intensities by reducing the determined radiation dose discrepancy.

According to one aspect, a method of radiotherapy re-planning can include accessing, by one or more processors, patient specific data of a patient. The patient specific data can include one or more parameters of an anatomical region of the patient, and the anatomical region can include a planning target volume (PTV) for which radiation to be applied and one or more anatomical sub-regions corresponding to normal tissues. The method can include the one or more processors determining a re-mapped influence matrix based on an initial influence matrix and anatomical changes. The method can include the one or more processors determining radiation machine settings using the re-mapped influence matrix.

According to one other aspect, a radiotherapy re-planning system can include one or more processors and a memory to store computer code instructions. The computer code instructions, when executed cause, the one or more processors to access patient specific data of a patient. The patient specific data can include one or more parameters of an anatomical region of the patient, and the anatomical region can include a planning target volume (PTV) for which radiation to be applied and one or more anatomical sub-regions corresponding to normal tissues. The one or more processors can determine a re-mapped influence matrix based on an initial influence matrix and anatomical changes to the anatomical region. The one or more processors can determine one or more radiation machine settings using the re-mapped influence matrix.

According to yet one other aspect, a computer readable medium can include computer code instructions stored thereon. The computer code instructions when executed cause one or more processors to perform a method that includes accessing, by one or more processors, patient specific data of a patient. The patient specific data can include one or more parameters of an anatomical region of the patient, and the anatomical region can include a planning target volume (PTV) for which radiation to be applied and one or more anatomical sub-regions corresponding to normal tissues. The method can include the one or more processors determining a re-mapped influence matrix based on an initial influence matrix and anatomical changes. The method can include the one or more processors determining radiation machine settings using the re-mapped influence matrix.

DETAILED DESCRIPTION

For purposes of reading the description of the various embodiments below, the following descriptions of the sections of the specification and their respective contents may be helpful:

Section A describes a computing and network environment which may be useful for practicing embodiments described herein.

Section B describes an embodiment of an improved radiation treatment planning system.

Section C describes systems and methods for automatic IMRT treatment planning.

Section D describes systems and methods for automatic VMAT treatment planning.

Section E describes systems and methods for radiotherapy re-planning.

A. Computing and Network Environment

Figure 1A:
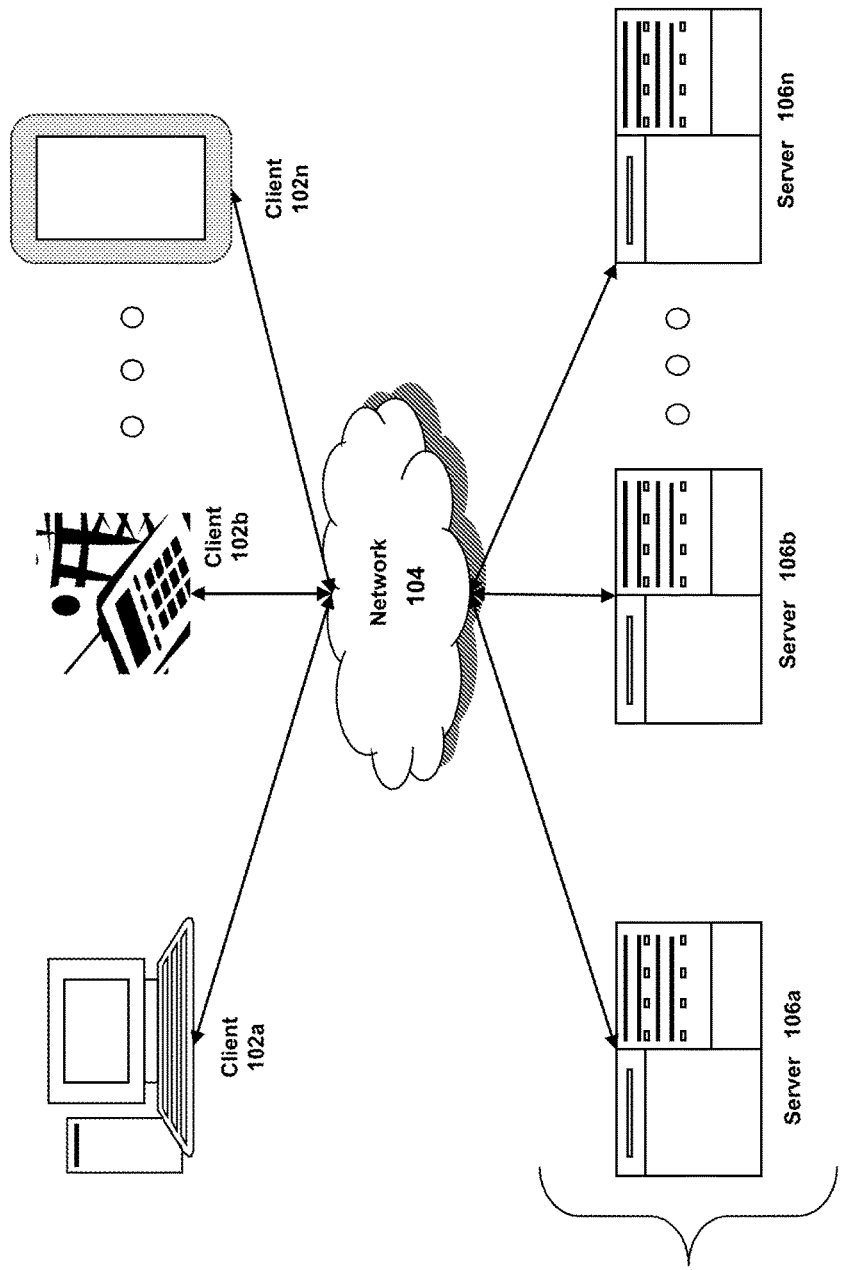
FIG. 1A is a block diagram depicting an embodiment of a computing and network environment.

In addition to discussing specific embodiments of the present solution, it may be helpful to describe aspects of the operating environment as well as associated system components (e.g., hardware elements) in connection with the methods and systems described herein. Referring to FIG. 1A, an embodiment of a computing and network environment 10 is depicted. In brief overview, the computing and network environment includes one or more clients 102a-102n (also generally referred to as local machine(s) 102, client(s) 102, client node(s) 102, client machine(s) 102, client computer(s) 102, client device(s) 102, endpoint(s) 102, or endpoint node(s) 102) in communication with one or more servers 106a-106n (also generally referred to as server(s) 106, node 106, or remote machine(s) 106) via one or more networks 104. In some embodiments, a client 102 has the capacity to function as both a client node seeking access to resources provided by a server and as a server providing access to hosted resources for other clients 102a-102n.

Although FIG. 1A shows a network 104 between the clients 102 and the servers 106, the clients 102 and the servers 106 may be on the same network 104. In some embodiments, there are multiple networks 104 between the clients 102 and the servers 106. In one of these embodiments, a network 104' (not shown) may be a private network and a network 104 may be a public network. In another of these embodiments, a network 104 may be a private network and a network 104' a public network. In still another of these embodiments, networks 104 and 104' may both be private networks.

The network 104 may be connected via wired or wireless links. Wired links may include Digital Subscriber Line (DSL), coaxial cable lines, or optical fiber lines. The wireless links may include BLUETOOTH, Wi-Fi, Worldwide Interoperability for Microwave Access (WiMAX), an infrared channel or satellite band. The wireless links may also include any cellular network standards used to communicate among mobile devices, including standards that qualify as 1G, 2G, 3G, or 4G. The network standards may qualify as one or more generation of mobile telecommunication standards by fulfilling a specification or standards such as the specifications maintained by International Telecommunication Union. The 3G standards, for example, may correspond to the International Mobile Telecommunications-2000 (IMT-2000) specification, and the 1G standards may correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards may use various channel access methods e.g. FDMA, TDMA, CDMA, or SDMA. In some embodiments, different types of data may be transmitted via different links and standards. In other embodiments, the same types of data may be transmitted via different links and standards.

The network 104 may be any type and/or form of network. The geographical scope of the network 104 may vary widely and the network 104 can be a body area network (BAN), a personal area network (PAN), a local-area network (LAN), e.g. Intranet, a metropolitan area network (MAN), a wide area network (WAN), or the Internet. The topology of the network 104 may be of any form and may include, e.g., any of the following: point-to-point, bus, star, ring, mesh, or tree. The network 104 may be an overlay network which is virtual and sits on top of one or more layers of other networks 104'. The network 104 may be of any such network topology as known to those ordinarily skilled in the art capable of supporting the operations described herein. The network 104 may utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite may include application layer, transport layer, internet layer (including, e.g., IPv6), or the link layer. The network 104 may be a type of a broadcast network, a telecommunications network, a data communication network, or a computer network.

In some embodiments, the computing and network environment 10 may include multiple, logically-grouped servers 106. In one of these embodiments, the logical group of servers may be referred to as a server farm 38 or a machine farm 38. In another of these embodiments, the servers 106 may be geographically dispersed. In other embodiments, a machine farm 38 may be administered as a single entity. In still other embodiments, the machine farm 38 includes a plurality of machine farms 38. The servers 106 within each machine farm 38 can be heterogeneous-one or more of the servers 106 or machines 106 can operate according to one type of operating system platform (e.g., WINDOWS 8 or 10, manufactured by Microsoft Corp. of Redmond, Washington), while one or more of the other servers 106 can operate on according to another type of operating system platform (e.g., Unix, Linux, or Mac OS X).

In one embodiment, servers 106 in the machine farm 38 may be stored in high-density rack systems, along with associated storage systems, and located in an enterprise data center. In this embodiment, consolidating the servers 106 in this way may improve system manageability, data security, the physical security of the system, and system performance by locating servers 106 and high performance storage systems on localized high performance networks. Centralizing the servers 106 and storage systems and coupling them with advanced system management tools allows more efficient use of server resources.

The servers 106 of each machine farm 38 do not need to be physically proximate to another server 106 in the same machine farm 38. Thus, the group of servers 106 logically grouped as a machine farm 38 may be interconnected using a wide-area network (WAN) connection or a metropolitan-area network (MAN) connection. For example, a machine farm 38 may include servers 106 physically located in different continents or different regions of a continent, country, state, city, campus, or room. Data transmission speeds between servers 106 in the machine farm 38 can be increased if the servers 106 are connected using a local-area network (LAN) connection or some form of direct connection. Additionally, a heterogeneous machine farm 38 may include one or more servers 106 operating according to a type of operating system, while one or more other servers 106 execute one or more types of hypervisors rather than operating systems. In these embodiments, hypervisors may be used to emulate virtual hardware, partition physical hardware, virtualize physical hardware, and execute virtual machines that provide access to computing environments, allowing multiple operating systems to run concurrently on a host computer. Native hypervisors may run directly on the host computer. Hypervisors may include VMware ESX/ESXi, manufactured by VMWare, Inc., of Palo Alto, California; the Xen hypervisor, an open source product whose development is overseen by Citrix Systems, Inc.; the HYPER-V hypervisors provided by Microsoft or others. Hosted hypervisors may run within an operating system on a second software level. Examples of hosted hypervisors may include VMware Workstation and VIRTUALBOX.

Management of the machine farm 38 may be de-centralized. For example, one or more servers 106 may comprise components, subsystems and modules to support one or more management services for the machine farm 38. In one of these embodiments, one or more servers 106 provide functionality for management of dynamic data, including techniques for handling failover, data replication, and increasing the robustness of the machine farm 38. Each server 106 may communicate with a persistent store and, in some embodiments, with a dynamic store.

Server 106 may be a file server, application server, web server, proxy server, appliance, network appliance, gateway, gateway server, virtualization server, deployment server, SSL VPN server, firewall, Internet of Things (IoT) controller. In one embodiment, the server 106 may be referred to as a remote machine or a node. In another embodiment, a plurality of nodes 290 may be in the path between any two communicating servers.

Figure 1B:
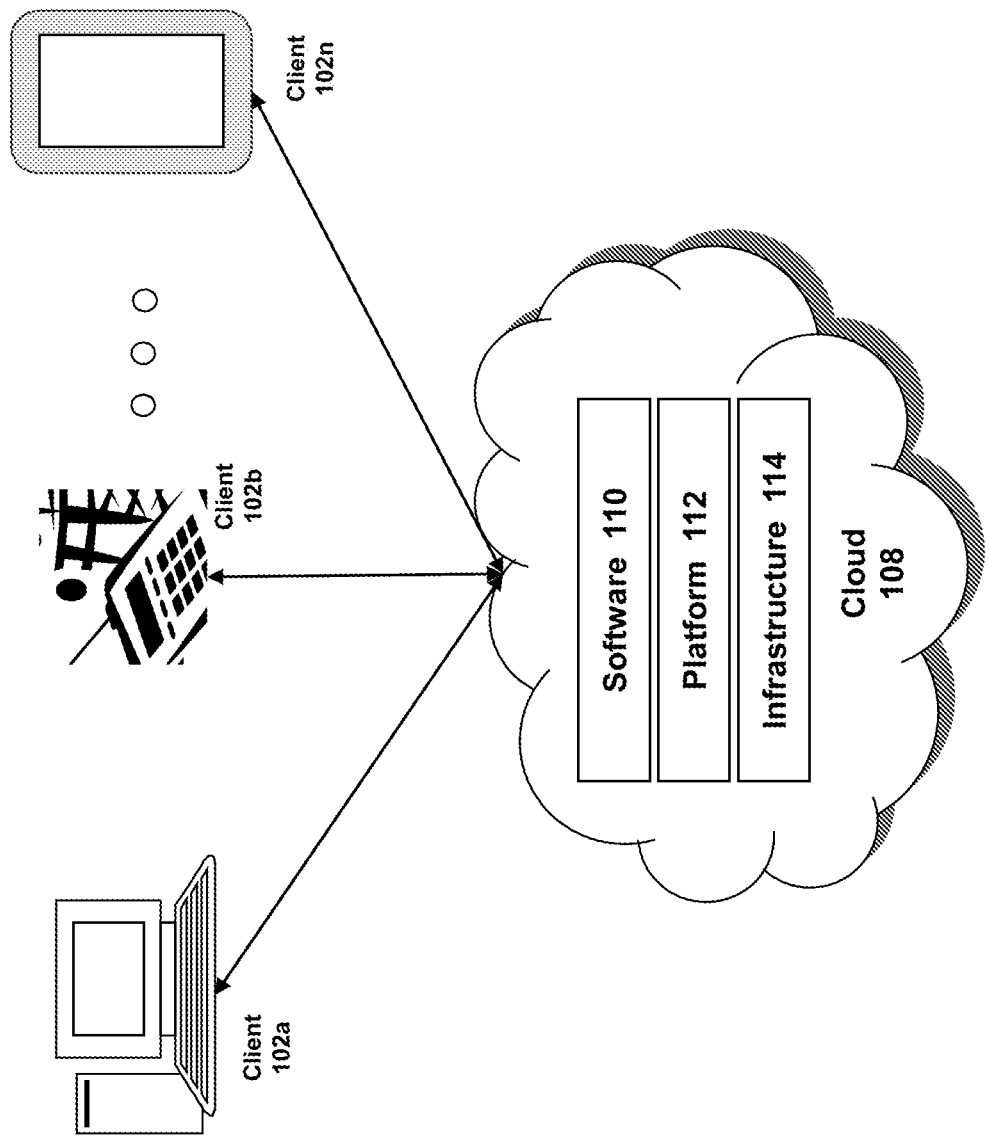
FIGS. 1B-1D are block diagrams depicting embodiments of computers useful in connection with the methods and systems described herein.

Referring to FIG. 1B, a cloud computing environment is depicted. The cloud computing environment can be part of the computing and network environment 10. A cloud computing environment may provide client 102 with one or more resources provided by the computing and network environment 10. The cloud computing environment may include one or more clients 102a-102n, in communication with the cloud 108 over one or more networks 104. Clients 102 may include, e.g., thick clients, thin clients, and zero clients. A thick client may provide at least some functionality even when disconnected from the cloud 108 or servers 106. A thin client or a zero client may depend on the connection to the cloud 108 or server 106 to provide functionality. A zero client may depend on the cloud 108 or other networks 104 or servers 106 to retrieve operating system data for the client device. The cloud 108 may include back end platforms, e.g., servers 106, storage, server farms or data centers.

The cloud 108 may be public, private, or hybrid. Public clouds may include public servers 106 that are maintained by third parties to the clients 102 or the owners of the clients. The servers 106 may be located off-site in remote geographical locations as disclosed above or otherwise. Public clouds may be connected to the servers 106 over a public network. Private clouds may include private servers 106 that are physically maintained by clients 102 or owners of clients. Private clouds may be connected to the servers 106 over a private network 104. Hybrid clouds 108 may include both the private and public networks 104 and servers 106.

The cloud 108 may also include a cloud based delivery, e.g. Software as a Service (SaaS) 110, Platform as a Service (PaaS) 112, and Infrastructure as a Service (IaaS) 114. IaaS may refer to a user renting the use of infrastructure resources that are needed during a specified time period. IaaS providers may offer storage, networking, servers or virtualization resources from large pools, allowing the users to quickly scale up by accessing more resources as needed. Examples of IaaS include AMAZON WEB SERVICES provided by Amazon.com, Inc., of Seattle, Washington, RACKSPACE CLOUD provided by Rackspace US, Inc., of San Antonio, Texas, Google Compute Engine provided by Google Inc. of Mountain View, California, or RIGHTSCALE provided by RightScale, Inc., of Santa Barbara, California. PaaS providers may offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Washington, Google App Engine provided by Google Inc., and HEROKU provided by Heroku, Inc. of San Francisco, California. SaaS providers may offer the resources that PaaS provides, including storage, networking, servers, virtualization, operating system, middleware, or runtime resources. In some embodiments, SaaS providers may offer additional resources including, e.g., data and application resources. Examples of SaaS include GOOGLE APPS provided by Google Inc., SALESFORCE provided by Salesforce.com Inc. of San Francisco, California, or OFFICE 365 provided by Microsoft Corporation. Examples of SaaS may also include data storage providers, e.g. DROPBOX provided by Dropbox, Inc. of San Francisco, California, Microsoft SKYDRIVE provided by Microsoft Corporation, Google Drive provided by Google Inc., or Apple ICLOUD provided by Apple Inc. of Cupertino, California.

Clients 102 may access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards may allow clients access to resources over HTTP, and may use Representational State Transfer (REST) protocol or Simple Object Access Protocol (SOAP). Clients 102 may access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that may be built on REST, HTTP, XML, or other protocols. Clients 102 may access SaaS resources through the use of web-based user interfaces, provided by a web browser (e.g. GOOGLE CHROME, Microsoft INTERNET EXPLORER, or Mozilla Firefox provided by Mozilla Foundation of Mountain View, California). Clients 102 may also access SaaS resources through smartphone or tablet applications, including, for example, Salesforce Sales Cloud, or Google Drive app. Clients 102 may also access SaaS resources through the client operating system, including, e.g., Windows file system for DROPBOX.

In some embodiments, access to IaaS, PaaS, or SaaS resources may be authenticated. For example, a server or authentication server may authenticate a user via security certificates, HTTPS, or API keys. API keys may include various encryption standards such as, e.g., Advanced Encryption Standard (AES). Data resources may be sent over Transport Layer Security (TLS) or Secure Sockets Layer (SSL).

Figure 1C:
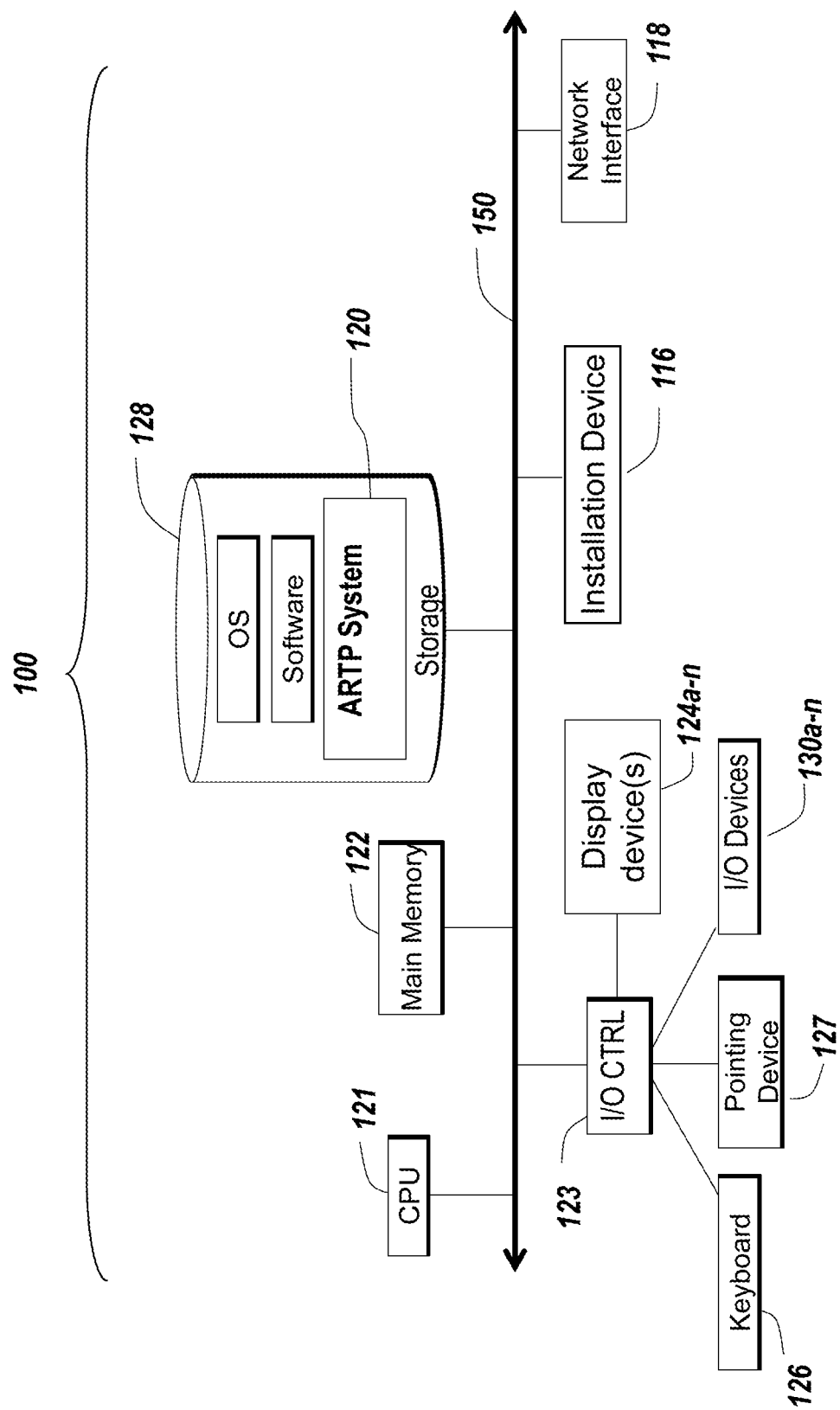
Figure 1D:
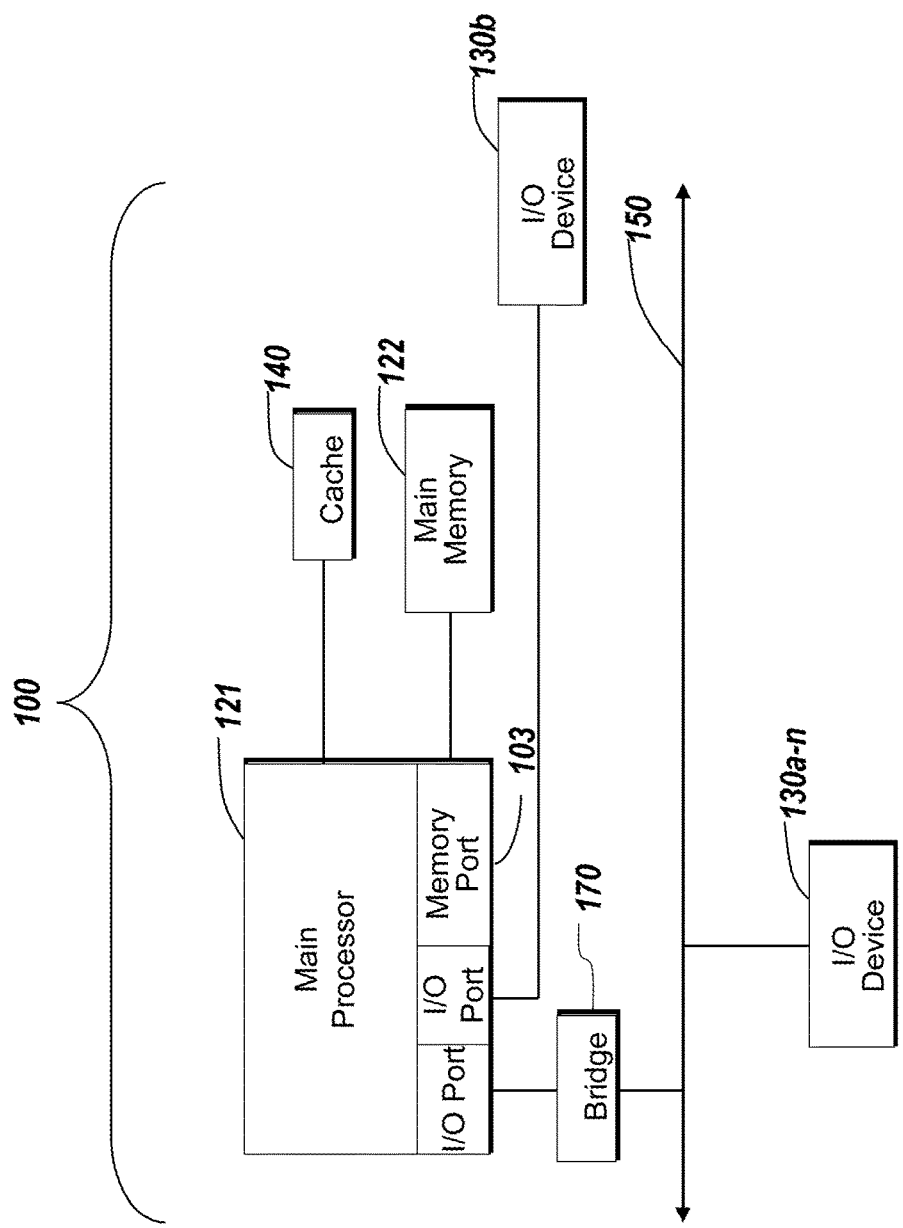

The client 102 and server 106 may be deployed as and/or executed on any type and form of computing device, e.g. a computer, network device or appliance capable of communicating on any type and form of network and performing the operations described herein. FIGS. 1C and 1D depict block diagrams of a computing device 100 useful for practicing an embodiment of the client 102 or a server 106. As shown in FIGS. 1C and 1D, each computing device 100 includes a central processing unit 121, and a main memory unit 122. As shown in FIG. 1C, a computing device 100 may include a storage device 128, an installation device 116, a network interface 118, an I/O controller 123, display devices 124a-124n, a keyboard 126 and a pointing device 127, e.g. a mouse. The storage device 128 may include, without limitation, an operating system, software, and a software of an automatic radiation treatment planning (ARTPS) system 120. As shown in FIG. 1D, each computing device 100 may also include additional optional elements, e.g. a memory port 103, a bridge 170, one or more input/output devices 130a-130n (generally referred to using reference numeral 130), and a cache memory 140 in communication with the central processing unit 121.

The central processing unit 121 is any logic circuitry that responds to and processes instructions fetched from the main memory unit 122. In many embodiments, the central processing unit 121 is provided by a microprocessor unit, e.g.: those manufactured by Intel Corporation of Mountain View, California; those manufactured by Motorola Corporation of Schaumburg, Illinois; the ARM processor and TEGRA system on a chip (SoC) manufactured by Nvidia of Santa Clara, California; the POWER7 processor, those manufactured by International Business Machines of White Plains, New York; or those manufactured by Advanced Micro Devices of Sunnyvale, California. The computing device 100 may be based on any of these processors, or any other processor capable of operating as described herein. The central processing unit 121 may utilize instruction level parallelism, thread level parallelism, different levels of cache, and multi-core processors. A multi-core processor may include two or more processing units on a single computing component. Examples of a multi-core processors include the AMD PHENOM IIX2, INTEL CORE i5 and INTEL CORE i7.

Main memory unit 122 may include one or more memory chips capable of storing data and allowing any storage location to be directly accessed by the microprocessor 121. Main memory unit 122 may be volatile and faster than storage 128 memory. Main memory units 122 may be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 122 or the storage 128 may be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 122 may be based on any of the above described memory chips, or any other available memory chips capable of operating as described herein. In the embodiment shown in FIG. 1C, the processor 121 communicates with main memory 122 via a system bus 150 (described in more detail below). FIG. 1D depicts an embodiment of a computing device 100 in which the processor communicates directly with main memory 122 via a memory port 103. For example, in FIG. 1D the main memory 122 may be DRDRAM.

FIG. 1D depicts an embodiment in which the main processor 121 communicates directly with cache memory 140 via a secondary bus, sometimes referred to as a backside bus. In other embodiments, the main processor 121 communicates with cache memory 140 using the system bus 150. Cache memory 140 typically has a faster response time than main memory 122 and is typically provided by SRAM, BSRAM, or EDRAM. In the embodiment shown in FIG. 1D, the processor 121 communicates with various I/O devices 130 via a local system bus 150. Various buses may be used to connect the central processing unit 121 to any of the I/O devices 130, including a PCI bus, a PCI-X bus, or a PCI-Express bus, or a NuBus. For embodiments in which the I/O device is a video display 124, the processor 121 may use an Advanced Graphics Port (AGP) to communicate with the display 124 or the I/O controller 123 for the display 124. FIG. 1D depicts an embodiment of a computer 100 in which the main processor 121 communicates directly with I/O device 130b or other processors 121' via HYPERTRANSPORT, RAPIDIO, or INFINIBAND communications technology. FIG. 1D also depicts an embodiment in which local busses and direct communication are mixed: the processor 121 communicates with I/O device 130a using a local interconnect bus while communicating with I/O device 130b directly.

A wide variety of I/O devices 130a-130n may be present in the computing device 100. Input devices may include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, and 3D printers.

Devices 130a-130n may include a combination of multiple input or output devices, including, e.g., Microsoft KINECT, Nintendo Wiimote for the WII, Nintendo WII U GAMEPAD, or Apple IPHONE. Some devices 130a-130n allow gesture recognition inputs through combining some of the inputs and outputs. Some devices 130a-130n provides for facial recognition which may be utilized as an input for different purposes including authentication and other commands. Some devices 130a-130n provides for voice recognition and inputs, including, e.g., Microsoft KINECT, SIRI for IPHONE by Apple, Google Now or Google Voice Search.

Additional devices 130a-130n have both input and output capabilities, including, e.g., haptic feedback devices, touchscreen displays, or multi-touch displays. Touchscreen, multi-touch displays, touchpads, touch mice, or other touch sensing devices may use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, e.g., pinch, spread, rotate, scroll, or other gestures. Some touchscreen devices, including, e.g., Microsoft PIXELSENSE or Multi-Touch Collaboration Wall, may have larger surfaces, such as on a table-top or on a wall, and may also interact with other electronic devices. Some I/O devices 130a-130n, display devices 124a-124n or group of devices may be augment reality devices. The I/O devices may be controlled by an I/O controller 123 as shown in FIG. 1C. The I/O controller may control one or more I/O devices, such as, e.g., a keyboard 126 and a pointing device 127, e.g., a mouse or optical pen. Furthermore, an I/O device may also provide storage and/or an installation medium 116 for the computing device 100. In still other embodiments, the computing device 100 may provide USB connections (not shown) to receive handheld USB storage devices. In further embodiments, an I/O device 130 may be a bridge between the system bus 150 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 124a-124n may be connected to I/O controller 123. Display devices may include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays may use, e.g. stereoscopy, polarization filters, active shutters, or autostereoscopy. Display devices 124a-124n may also be a head-mounted display (HMD). In some embodiments, display devices 124a-124n or the corresponding I/O controllers 123 may be controlled through or have hardware support for OPENGL or DIRECTX API or other graphics libraries.

In some embodiments, the computing device 100 may include or connect to multiple display devices 124a-124n, which each may be of the same or different type and/or form. As such, any of the I/O devices 130a-130n and/or the I/O controller 123 may include any type and/or form of suitable hardware, software, or combination of hardware and software to support, enable or provide for the connection and use of multiple display devices 124a-124n by the computing device 100. For example, the computing device 100 may include any type and/or form of video adapter, video card, driver, and/or library to interface, communicate, connect or otherwise use the display devices 124a-124n. In one embodiment, a video adapter may include multiple connectors to interface to multiple display devices 124a-124n. In other embodiments, the computing device 100 may include multiple video adapters, with each video adapter connected to one or more of the display devices 124a-124n. In some embodiments, any portion of the operating system of the computing device 100 may be configured for using multiple displays 124a-124n. In other embodiments, one or more of the display devices 124a-124n may be provided by one or more other computing devices 100a or 100b connected to the computing device 100, via the network 104. In some embodiments software may be designed and constructed to use another computer's display device as a second display device 124a for the computing device 100. For example, in one embodiment, an Apple iPad may connect to a computing device 100 and use the display of the device 100 as an additional display screen that may be used as an extended desktop. One ordinarily skilled in the art will recognize and appreciate the various ways and embodiments that a computing device 100 may be configured to have multiple display devices 124a-124n.

Figure 7:
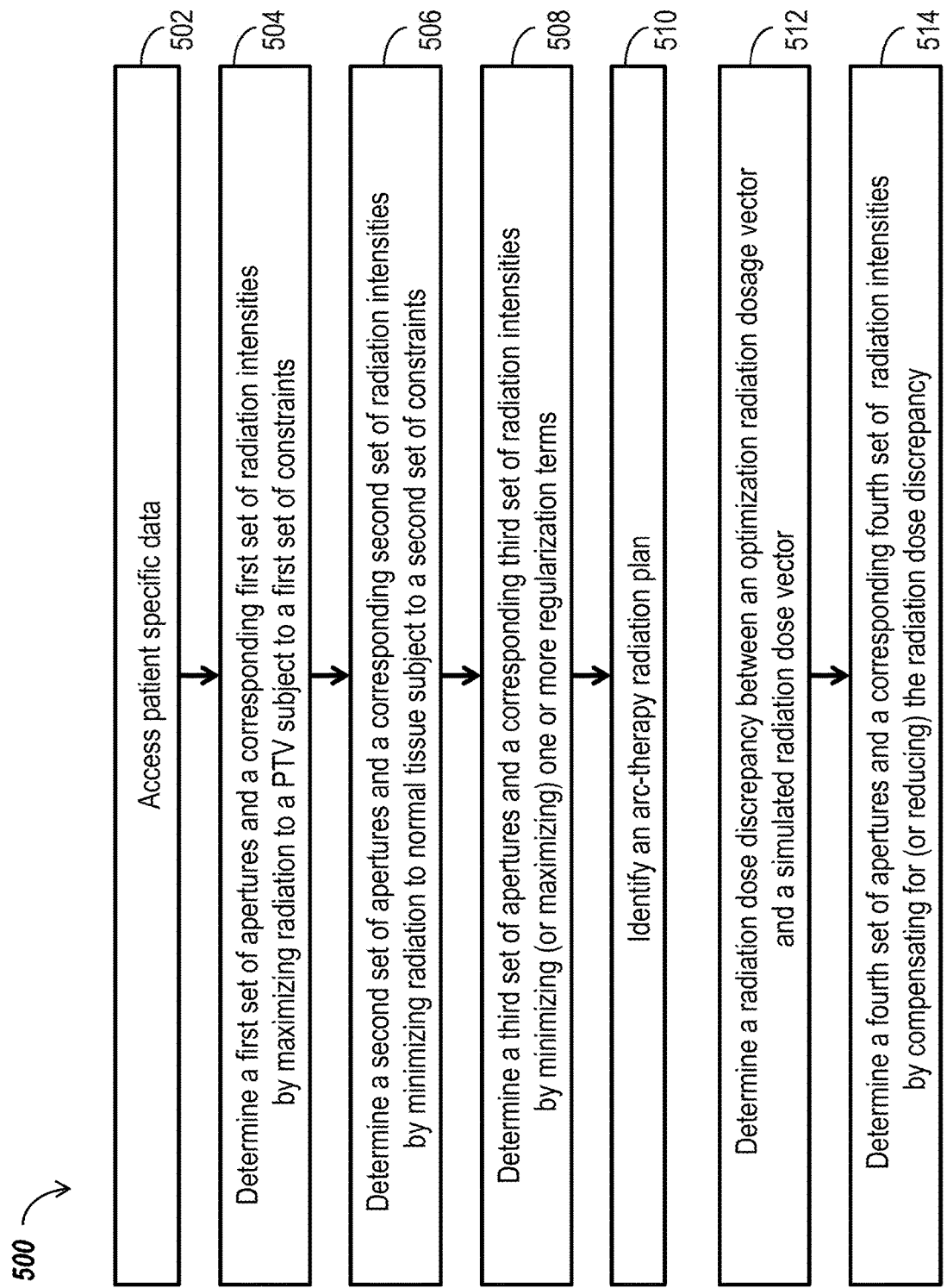
FIG. 7 shows a flowchart illustrating a method of volumetric modulated arc therapy (VMAT) treatment planning, according to inventive concepts of this disclosure.

Referring again to FIG. 1C, the computing device 100 may comprise a storage device 128 (e.g. one or more hard disk drives or redundant arrays of independent disks) for storing an operating system or other related software, and for storing application software programs such as any computer code programs related to the software for the ARTP system 120. The ARTP system 120 can include computer code programs for executing any of the methods described herein, such as the methods described with regard to FIGS. 3 and 7. Examples of storage device 128 include, e.g., hard disk drive (HDD); optical drive including CD drive, DVD drive, or BLU-RAY drive; solid-state drive (SSD); USB flash drive; or any other device suitable for storing data. Some storage devices may include multiple volatile and non-volatile memories, including, e.g., solid state hybrid drives that combine hard disks with solid state cache. Some storage device 128 may be non-volatile, mutable, or read-only. Some storage device 128 may be internal and connect to the computing device 100 via a bus 150. Some storage device 128 may be external and connect to the computing device 100 via a I/O device 130 that provides an external bus. Some storage device 128 may connect to the computing device 100 via the network interface 118 over a network 104, including, e.g., the Remote Disk for MACBOOK AIR by Apple. Some client devices 100 may not require a non-volatile storage device 128 and may be thin clients or zero clients 102. Some storage device 128 may also be used as an installation device 116, and may be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Client device 100 may also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc. An application distribution platform may facilitate installation of software on a client device 102. An application distribution platform may include a repository of applications on a server 106 or a cloud 108, which the clients 102a-102n may access over a network 104. An application distribution platform may include application developed and provided by various developers. A user of a client device 102 may select, purchase and/or download an application via the application distribution platform.

Furthermore, the computing device 100 may include a network interface 118 to interface to the network 104 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 100 communicates with other computing devices 100' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Florida. The network interface 118 may comprise a built-in network adapter, network interface card, PCMCIA network card, EXPRESSCARD network card, card bus network adapter, wireless network adapter, USB network adapter, modem or any other device suitable for interfacing the computing device 100 to any type of network capable of communication and performing the operations described herein.

A computing device 100 of the sort depicted in FIGS. 1B and 1C may operate under the control of an operating system, which controls scheduling of tasks and access to system resources. The computing device 100 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Washington; MAC OS and iOS, manufactured by Apple, Inc. of Cupertino, California; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, California, among others. Some operating systems, including, e.g., the CHROME OS by Google, may be used on zero clients or thin clients, including, e.g., CHROMEBOOKS.

The computer system 100 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 100 has sufficient processor power and memory capacity to perform the operations described herein. In some embodiments, the computing device 100 may have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 100 is a gaming system. For example, the computer system 100 may comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, an XBOX 360 device manufactured by the Microsoft Corporation of Redmond, Washington.

In some embodiments, the computing device 100 is a digital audio player such as the Apple IPOD, IPOD Touch, and IPOD NANO lines of devices, manufactured by Apple Computer of Cupertino, California. Some digital audio players may have other functionality, including, e.g., a gaming system or any functionality made available by an application from a digital application distribution platform. For example, the IPOD Touch may access the Apple App Store. In some embodiments, the computing device 100 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the computing device 100 is a tablet e.g. the IPAD line of devices by Apple; GALAXY TAB family of devices by Samsung; or KINDLE FIRE, by Amazon.com, Inc. of Seattle, Washington. In other embodiments, the computing device 100 is a eBook reader, e.g. the KINDLE family of devices by Amazon.com, or NOOK family of devices by Barnes & Noble, Inc. of New York City, New York.

In some embodiments, the communications device 102 includes a combination of devices, e.g. a smartphone combined with a digital audio player or portable media player. For example, one of these embodiments is a smartphone, e.g. the IPHONE family of smartphones manufactured by Apple, Inc.; a Samsung GALAXY family of smartphones manufactured by Samsung, Inc.; or a Motorola DROID family of smartphones. In yet another embodiment, the communications device 102 is a laptop or desktop computer equipped with a web browser and a microphone and speaker system, e.g. a telephony headset. In these embodiments, the communications devices 102 are web-enabled and can receive and initiate phone calls. In some embodiments, a laptop or desktop computer is also equipped with a webcam or other video capture device that enables video chat and video call.

In some embodiments, the status of one or more machines 102, 106 in the network 104 is monitored, generally as part of network management. In one of these embodiments, the status of a machine may include an identification of load information (e.g., the number of processes on the machine, central processing unit (CPU) and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

B. An Improved Radiation Treatment Planning System

Treatment planning is a time-consuming and resource-demanding process or task that plays an important role in improving the quality and the likelihood of success of radiation treatment therapy. Identifying a radiation plan that accurately targets cancerous cells while sparing healthy cells (or normal tissue) for a given patient can increase a patient's chances for cure and recovery and avoid or mitigate undesired side effects. For each patient, the respective radiation plan usually depends on patient specific data (or patient specific parameters), such as the type, location and geometry (e.g., shape, and size) of the patient's tumor, the type, location and geometry of organs and tissues around the tumor (or in the path of any potential radiation beam), or a combination thereof. Having a treatment planner perform radiation treatment planning manually makes the radiation treatment planning process time consuming and the quality of resulting treatment plans heavily dependent on the planner's skills and experience. Furthermore, considering the complexity of the goals to be achieved and the constraints to be satisfied (e.g., the radiation dose to be applied to the tumor, and the healthy organs or normal tissues to be avoided or for which radiation to be mitigated), treatment plans developed by human planners may not be optimal or near optimal with regard to accurately targeting cancerous cells and avoiding healthy anatomical regions.

Patient specific parameters (or data), such as the location and geometry of various organs or tissues around the tumor as well as the geometry and relative location (e.g., relative to neighboring organs or tissues) of the tumor can be depicted in medical images (e.g., generated using X-rays, magnetic resonance imaging (MRI), ultrasound imaging, electrical impedance tomography, optical tomography, or a combination thereof) of the patient or an anatomical region thereof. A physician, such as a radiologist, can mark (e.g., contour) the tumor and/or other organs or tissues of interest in the medical images of the patient. Once all the organs of interest are contoured by a physician, a planner uses treatment planning system (TPS) to optimize radiation machine parameters and create a radiation treatment plan that meets specific clinical criteria (e.g., the radiation dose to be applied to the tumor as well as the maximum radiation dose that can be applied to each healthy (or normal) tissue or organ around the tumor). The planner typically carries the process of creating or developing a radiation treatment plan in a trial-and-error fashion. The planner can define a set of objective functions and penalty parameters associated with the tissues, organs, structures or anatomical sub-regions of interest and then run an optimization problem to estimate various parameters associated with the radiation treatment plan. The planner can keep tweaking optimization parameters and re-running the optimization problem until a satisfactory radiation treatment plan is reached. Such trial-and-error approach can be time consuming and may not consistently lead to optimal or near-optimal radiation treatment plans.

Automating the radiation treatment planning process can speed up the process, enhance efficiency, for example, with respect to consumption of various resources, and make the radiation treatment plan quality consistent and independent of the planner's experience. However, for automated treatment planning processes, there is a tradeoff between radiation treatment plan accuracy on one side and processing speed and efficiency on another side. For instance, an automatic planning approach using constrained optimization, with clinical criteria formulated as hard constraints to be strictly enforced, can be time consuming since solving large-scale constrained optimization problems can take a long time. As used herein, hard constraints refer to constraints or conditions that are required to be enforced or satisfied. Soft constraints, on the other hand, are typically formulated as penalized terms in an objective function and are not guaranteed to be fully enforced. Furthermore, the way the planning problem is formulated can have a substantial impact on the speed and efficiency of the planning processing as well as the accuracy of the resulting radiation treatment plan(s).

In the current disclosure, systems and methods for improved automatic radiation treatment planning (ARTP) can employ hierarchical constrained optimization also referred to hereinafter as expedited hierarchical constrained optimization (ECHO). Specifically, the systems and methods described herein employ a combination of constrained optimization and a correction loop associated with unconstrained optimization to enhance the speed and efficiency of the radiation treatment planning process and improve the accuracy and quality of resulting radiation treatment plans. The use of a hierarchical constrained optimization approach (e.g., a sequence of constrained optimizations) leads to less complex and faster to solve (compared to a single more complex optimization problem) optimization problems. The correction loop allows for compensating for optimization error associated with the approximation techniques employed to speed up the process.

Figure 2:
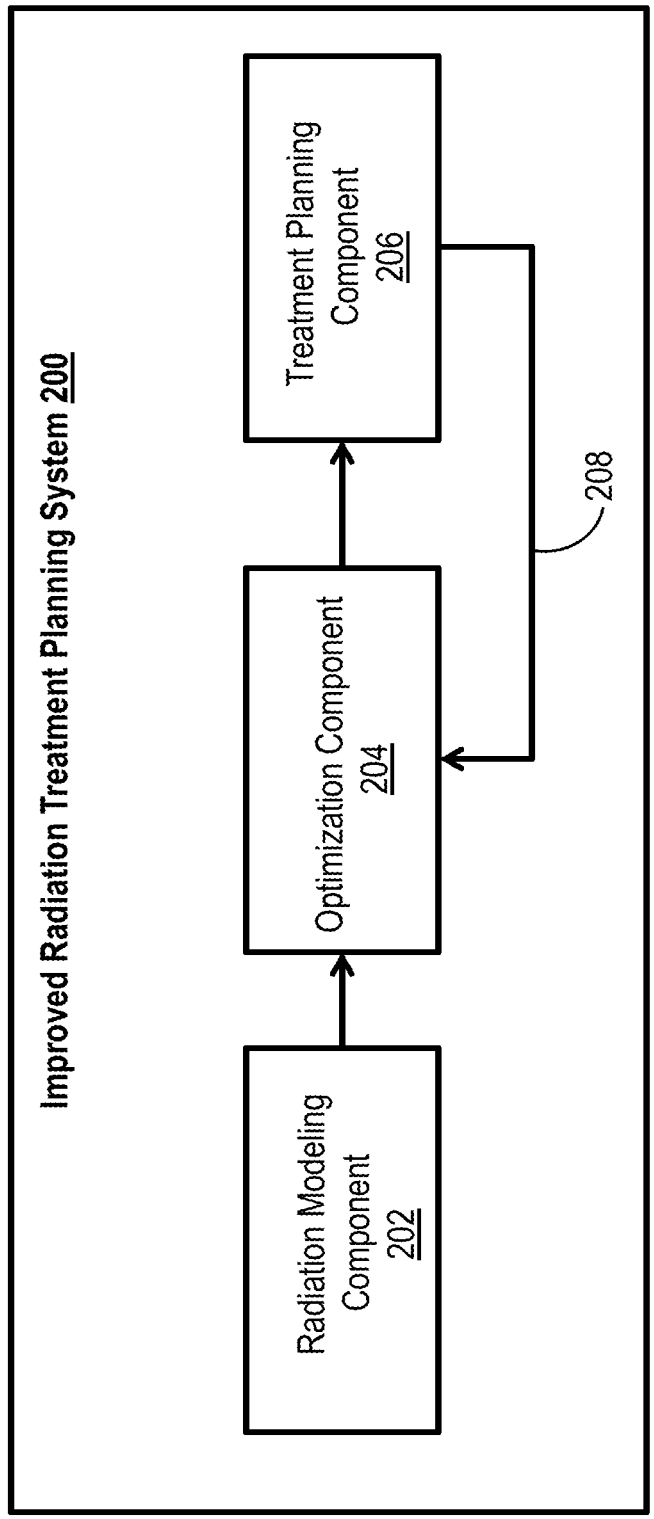
FIG. 2 is a block diagram illustrating an embodiment of an improved radiation treatment planning system, according to inventive concepts of this disclosure.

Referring to FIG. 2, a block diagram of an example improved radiation treatment planning system 200 is illustrated, according to inventive concepts of this disclosure. In brief overview, the radiation treatment planning system 200 can include a radiation modeling component 202, an optimization component 204, and a treatment planning component 206. The radiation treatment planning system 200 can also include a correction feedback loop allowing the treatment planning component 206 to feedback optimization error to the optimization component 208 for use in unconstrained optimization. The radiation treatment planning system 200 may further include input/output interfaces (not shown in FIG. 2) for receiving input data and providing output data to other systems or devices (e.g., a display device, a radiation machine, a remote database, or a combination thereof).

The radiation modeling component 202 can receive (e.g., via an input interface or from a memory) input data, such as medical images of a patient, indications of radiation angles, geometry parameters of a radiation machine, or a combination thereof, and determine or compute an influence matrix using the received input data. The influence matrix (also referred to hereinafter as influence matrix A) can be indicative of the radiation dose delivered to each voxel (of an anatomical region of interest) given a unit intensity for each radiation beamlet. Each row of the influence matrix A can correspond to a respective voxel of a plurality of voxels of the anatomical region of interest. Each column of the influence matrix A can correspond to a beamlet of a plurality of beamlets forming a radiation beam. The radiation modeling component 202 can store the determined or computed influence matrix A in a memory or database accessible by the optimization component 204.

The optimization component 204 can obtain the influence matric A, one or more prescription dose values (also referred to as desired or target radiation dose values), and data indicative of clinical criteria and/or respective parameters, (e.g., from a memory or database, or as user input). The target radiation dose values can include, for example, one or more radiation dose values to be applied to the tumor that are specified, for example, by a physician. The clinical criteria can include, for example, anatomical sub-regions (e.g., tissues or organs) to be avoided during the radiation treatment or maximum radiation doses associated with such anatomical sub-regions. The optimization component 204 can use the influence matric A, the prescription dose value(s), and the clinical criteria parameters to formulate and solve optimization problems, for example, to determine various estimates of a beamlet intensity vector defining a radiation beam. The optimization problems can include constrained and unconstrained optimization problems. Optimization problems solved by the optimization component 204 are described in further detail in the following sections below.

The treatment planning component 206 can receive one or more estimate of a beamlet intensity vector (or a radiation profile) from the optimization component 204, and determine various parameters (e.g., radiation dose to each voxel or organ, radiation machine parameters, or a combination thereof) using the received one or more estimates of the beamlet intensity vector. The treatment planning component 206 can determine (e.g., compute) a simulated (or fully simulated) radiation dose vector (or simulated radiation fluence map) using the received one or more estimates of a beamlet intensity vector (or a radiation profile). The treatment planning component 206 can feedback (as part of the feedback loop 208) the simulated (or fully simulated) radiation dose vector (or simulated radiation fluence map) to the optimization component 204. The optimization component 204 can determine (e.g., compute) dose discrepancy between an optimization radiation dose vector associated with the estimate of the beamlet intensity vector (e.g., equal to the influence matric multiplied by the estimate of the beamlet intensity vector) and the simulated radiation dose vector received from the treatment planning component 206. The optimization component 204 can determine an updated estimate of the beamlet intensity vector by minimizing (or reducing) the discrepancy, for example, using another optimization step. The treatment planning component 206 can determine final radiation treatment plan parameters for use by a radiation machine or for rendering by a display device, using the updated estimate of the beamlet intensity vector.

The treatment planning component 206 can determine the simulated radiation dose vector, for example, by determining (or computing) radiation treatment plan parameters based on the estimate of the beamlet intensity vector, and simulating the determined radiation treatment plan parameters. The dose discrepancy between the optimization radiation dose vector associated with the estimate of the beamlet intensity vector and the simulated radiation dose vector can be due to the fact that the optimization process (e.g., the influence matrix, the objective functions and the optimization constraints used by the optimization component 204 do not account for radiation leakage, radiation scatter, radiation sequencing effects or a combination thereof. For example, as the radiation source rotates around the patient's body and switches from one beam to another or from one beam aperture to another, the transitions may lead to some radiation errors not accounted for in the optimization process performed by the optimization component 204. Also radiation leakage can be due to non-perfect blocking of radiation at certain points of the radiation treatment process, and radiation scattering can be due to radiation beams scattering off aperture edges or other surfaces. In the case where the effects of such factors are accounted for in the influence matrix or in the optimization process, in general, the feedback loop, the computation of the dose discrepancy between the optimization radiation dose vector associated with the estimate of the beamlet intensity vector and the simulated radiation dose vector, and the additional optimization step can be omitted.

In some implementations, the treatment planning component 206 (alone or in combination with radiation modeling component 202) may be a conventional treatment planning system (TPS) while the optimization component 204 may be implemented as an application configured to interact with the TPS. The optimization component 204 and the treatment planning component 206 can be implemented to run on the same computing device 100 or on separate computing devices 100. The improved radiation treatment planning system 200 or components thereof can be implemented in radiation machine, a server 106, a client device, or other computing device.

C. Automated IMRT Planning

Figure 3:
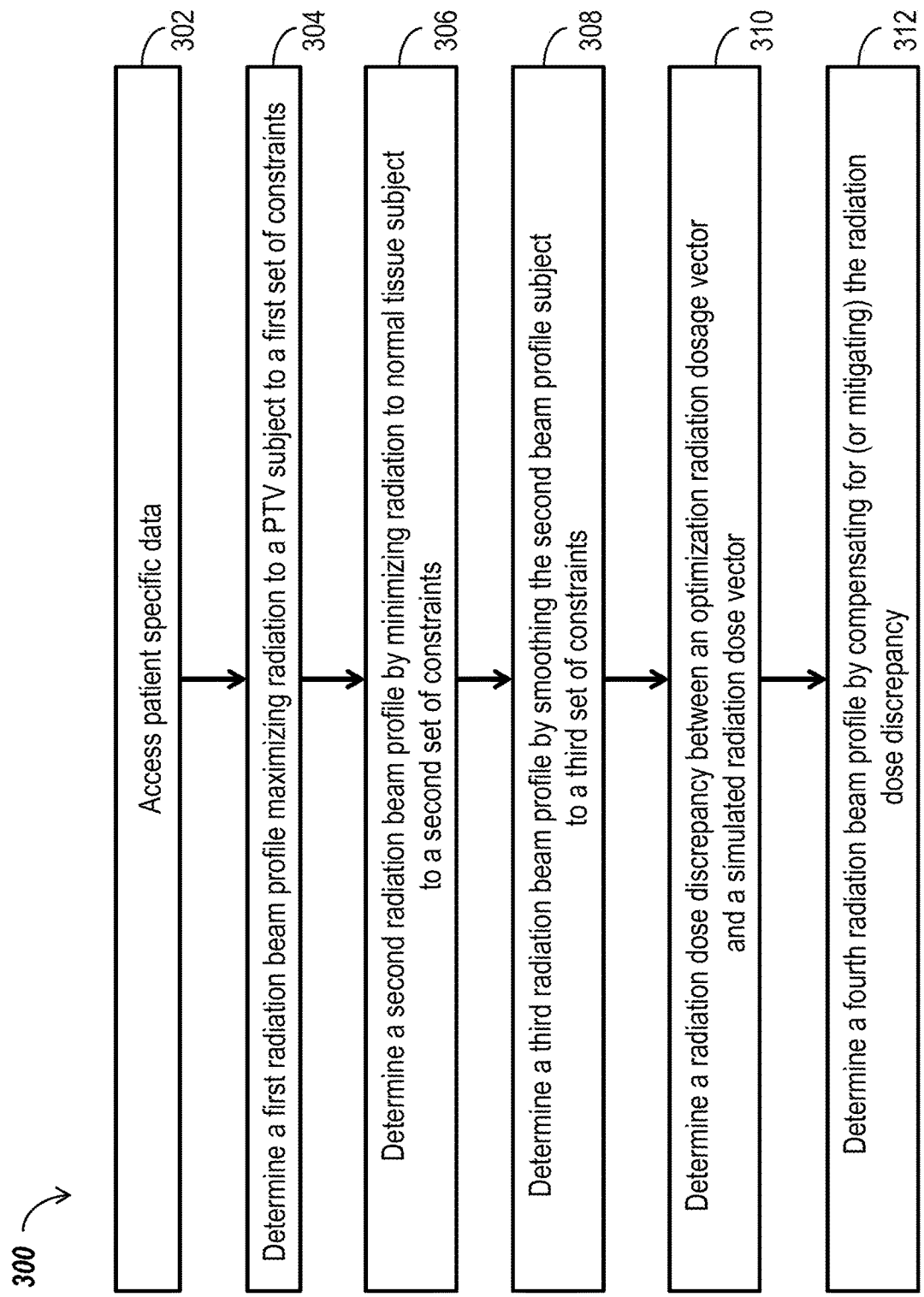
FIG. 3 shows a flowchart illustrating a method of intensity modulated radiation therapy (IMRT) treatment planning, according to inventive concepts of this disclosure.

Referring to FIG. 3, a flowchart illustrating a method 300 of intensity modulated radiation therapy (IMRT) treatment planning is shown, according to inventive concepts of this disclosure. In brief, the method 300 can include accessing patient specific data (BLOCK 302), and determining a first radiation beam profile maximizing radiation to a PTV subject to a first set of constraints (BLOCK 304). The method 300 can include determining a second radiation beam profile minimizing radiation to normal tissue subject to a second set of constraints (BLOCK 306). The method 300 can include determining a third radiation beam profile smoothing the second beam profile subject to a third set of constraints (BLOCK 308). The method 300 can include determining a radiation dose discrepancy between a radiation dose vector and a simulated dose vector (BLOCK 310), and determining a fourth radiation beam profile compensating for the determined radiation dose discrepancy (BLOCK 312).

The method 300 can include the optimization component 204 accessing patient specific data (BLOCK 302). A user can enter input data, for example, via an input interface, to a device associated with the radiation treatment planning system 200. The input data can include medical images of a patient, indications of radiation angles, data indicative of clinical criteria and/or respective parameters, a desired radiation dose, or a combination thereof. The medical images may include added contours (or other indications) for organs or structures of interest (e.g., tumors and/or sensitive organs around the tumors). For example, a physician can manually contour the organs or structures of interest on the medical images before providing the images as input data. The radiation modeling component 202 can use the medical images, the indications of the radiation angles, and/or other input data to calculate an influence matrix A specific to the patient. For modeling purposes, the radiation modeling component 202 can discretize the patient's body (or the imaged region thereof) into small cubical elements called voxels and discretize each radiation beam into small 2-dimensional elements called beamlets. The radiation modeling component 202 can calculate the radiation dose delivered to each voxel at the unit intensity of each beamlet and store the calculated radiation dose values into the matrix A. The rows and columns of the influence matrix A correspond to the voxels of the anatomical region described by the medical images and beamlets of potential radiating beams, respectively. The optimization component 204 can access the calculated influence matrix A, the desired radiation dose (e.g., prescribed radiation dose), and parameters indicative of (or associated with) clinical criteria or other optimization criteria from a memory or a database.

The method 300 can include the optimization component 204 determining a first radiation beam profile that maximizes radiation to a PTV (e.g., tumor) subject to a first set of constraints (BLOCK 304). The PTV can be defined in the medical images or via other input data (e.g., mask images). For example, the optimization component 204 can compute the first radiation beam profile (or radiation beam vector) by solving the optimization problem defined by equation (1) and the constraints (1.a) through (1.c) provided below:

$$X_1 = \min_x \sum_{s \in \{PTV\}} \|A^s x - p\|_2^2, \text{ subject to:} \quad (1)$$

$$\text{maximum}(A^s x) \leq d_s^{max}, s \in OARs \quad (1.a)$$

$$\text{mean}(A^s x) \leq d_s^{mean}, s \in OARs \quad (1.b)$$

$$x \geq 0. \quad (1.c)$$

In the formulation above, x represents a radiation beam profile (or a radiation beam vector) having entries that represent weights of the beamlets associated with the columns of the influence matrices $A^s$, where each influence matrix $A^s$ is associated with a respective OAR structure (e.g., organ) s. The parameter p represents the desired (also referred to as target or prescribed) radiation dose vector, and the parameters $d_s^{max}$ and $d_s^{mean}$ represent an upper bound limit of the maximum radiation dose and a mean radiation dose, respectively, for a specific OAR structure (e.g., organ) s. The objective function $F_1(x)=\Sigma_{s \in (PTV)}\|A^s x-p\|_2^2$ in equation (1) is used to minimize the deviation of the radiation dose $A^s x$ to the PTV from the desired (or prescription) dose p subject to the constraints (1.a) through (1.c). The maximum and mean dose constraints on all the structures s are enforced as hard constraints (1.a) and (1.b). The non-negativity of the radiation profile (or fluence map) is guaranteed by the constraint (1.c). The constraints (1.a) through (1.c) are hard constraints that are enforced by the optimization component 204.

Other optimization formulations for solving for the first radiation profile $X_1$ are contemplated by the current disclosure. For example, distinct desired/prescription radiation dose values (e.g., radiation dose values $p_s$) may be employed for different structures. Also, discrepancies between the radiation dose for each structure and the corresponding prescription radiation dose $p_s$ may be weighted differently in the objective function $F_1(x)$. Furthermore, another set of constraints different from the set of constraints (1.a) through (1.c) may be used.

The method 300 can include determining a second radiation beam profile that minimizes radiation to normal tissue subject to a second set of constraints (BLOCK 306). The optimization component 204 can determine the second radiation beam profile by solving the optimization problem below:

$$X_2 = \min_x \sum_{s \in OARs} gEUD(A^s x, a^s), \quad (2)$$

where $$gEUD(d, a) = \left( \frac{\sum_{i \in I} (d_i)^a}{card(d)} \right)^{\frac{1}{a}}, \text{ subject to:}$$

$$\max(A^s x) \le d_s^{max}, \quad (2.a)$$

$$\operatorname{mean}(A^s x) \le d_s^{mean}, \quad (2.b)$$

$$\|(A^s x - p)_+\|_2^2 \le \eta_s \|(A^s X_1 - p)_+\|_2^2 \text{ for } s \in \{PTV\}, \quad (2.c)$$

$$\|(p - A^s x)_+\|_2^2 \le \eta_s \|(p - A^s X_1)_+\|_2^2 \text{ for } s \in \{CTV, PTV - CTV\}, \quad (2.d)$$

and $$x \ge 0. \quad (2.e)$$

In the objective function $F_2(x)=\Sigma_{s \in OARs} gEUD(A^s x, a^s)$, the generalized equivalent uniform dose (gEUD) function is employed to minimize the radiation dose to the OARs. For each structure s, the optimization component 204 can select a corresponding input parameter a based on, for example, one or more clinical criteria (e.g., a=1 or 2 for parallel structures and a=10 or 15 for serial structures). The parameter $\eta_s$ represents a relaxation parameter (or slip parameter). Card(d) represents the cardinality of d.

The second set of constraints can include the first set of constraints (hard constraints (2.a), (2.b), and (2.e)) and additional new constraints (2.c) and (2.d). The additional new constraints (2.c) and (2.d) represent constraints in terms of the objective function $F_1(x)$ to preserve (within a relaxation parameter $\eta_s$) the radiation dose associated with the radiation beam profile $X_1$. In particular, the relaxation parameter ns in the constraints (2.c) and (2.d) is used to allow for limited deviation from the radiation dose associated with $X_1$ for, respectively, radiation over dose at the PTV and radiation under dose at a clinical target object (CTV) and at a region representing a difference between PTV and CTV (PTV-CTV). The operator(d)$_+$ in the constraints (2.c) and (2.d), represents the function max(d,0). The second radiation profile $X_2$ obtained using the optimization problem defined by equation (2) and the second set of constraints (2.a)-(2.e) allows for minimizing the radiation at the OARs without deviating substantially from the radiation dose associated with the first beam profile $X_1$.

The method 300 can include determining a third radiation beam profile smoothing the second radiation profile $X_2$ (BLOCK 308). The optimization component 204 can determine the third radiation profile, for example, by solving the optimization problem below:

$$X_3 = \min_x w_2 \sum_{b \in B} \left( \sum_{i \in I_b} (x_i - x_{R_i})^2 \right)^2 + \quad (3)$$

-continued $$w_2 \sum_{b \in B} \left( \sum_{i \in I_b} (x_i - x_{D_i})^2 \right)^2 \text{ subject to:}$$

$$\operatorname{maximum}(A^s x) \le d_s^{max}, \quad (3.a)$$

$$\operatorname{mean}(A^s x) \le d_s^{mean}, \quad (3.b)$$

$$\|(A^s x - p)_+\|_2^2 \le \eta_s^2 \|(A^s X_1 - p)_+\|_2^2 \text{ for } s \in \{PTV\}, \quad (3.c)$$

$$\|(p - A^s x)_+\|_2^2 \le \eta_s^2 \|(p - A^s X_1)_+\|_2^2 \text{ for } s \in \{CTV, PTV - CTV\}, \quad (3.d)$$

$$gEUD(A^s x, a^s) \le \eta_s \times gEUD(A^s X_2, a^s) \text{ for } s \in OARs, \quad (3.e)$$

and $$x \ge 0. \quad (3.f)$$

The parameters $w_1$ and $w_1$ represent weighting values applied to different terms in the objective function $F_3(x)=\Sigma_{b \in B}(\Sigma_{i \in I_b}(x_i - x_{R_i})^2)^2 + w_2 \Sigma_{b \in B}(\Sigma_{i \in I_b})(x_i - x_{D_i})^2)^2$. The parameters $x_{R_i}$ and $x_{D_i}$ represent neighboring beamlets to the beamlet $x_i$. For instance, the beamlet $x_{R_i}$ is indicative of the right neighbor beamlet to the beamlet $x_i$, and the beamlet $x_{D_i}$ is indicative of the down neighbor beamlet to the beamlet $x_i$. In some implementations, other neighbor beamlets can be used in the The constraints (3.a)-(3.d) and (3.f) are similar to the constraints (2.a)-(2.e) except for constraints (3.c) and (3.d) where a relaxation parameter ($\eta_s^2$) instead of $\eta_s$ is used. The new constraint (3.e) relaxes the terms $gEUD(A^s x, a^s)$ of the objective function $F_2(x)$ by the multiplicative relaxation parameter $\eta_s$ compared to the value of the same terms for the second radiation profile $X_2$. As such, the objective function values $F_2(X_3)$ and $F_2(X_2)$ can be forced to be relatively close to each other.

The optimization problem defined by equation (3) and the constraints (3.a)-(3.f) can smooth out the radiation beam profile using total variation metrics without significantly violating the optimization problems described by equations (1) and (2) and the corresponding constraints. Specifically, the optimization problems described by equations (1) and (2) are incorporated as constraints in the optimization problem defined by equation (3) and the constraints (3.a)-(3.f). The smoothing allows for efficient delivery of the radiation beam. The first term in the objective function $F_3(x)$ minimizes the total variation in the x-direction (leaf movement direction) and the second term accounts for the y-direction. Given that the smoothness in the leaf direction is more important, it makes sense to have $w_1 > w_2$. The smoothing can be viewed as spatial smoothing since the constraints (3.a)-(3.f) can smooth out deviation (or differences) between radiation intensities associated with radiation beams that are adjacent to each other along the rotational path of the radiation sources. The smoothing can be viewed as temporal smoothing since the constraints (3.a)-(3.f) can smooth out deviation (or differences) between radiation intensities associated with consecutive radiation beams during the radiation process.

The method 300 can include determining a radiation dose discrepancy between a radiation dose vector associated with the third radiation beam profile and a simulated dose vector calculated by the treatment planning system using the third radiation beam profile (BLOCK 310). The optimization component 204 can provide the third radiation beam profile $X_3$ to the treatment planning component 206. The treatment planning component 206 can use the third radiation beam profile $X_3$ to determine the simulated radiation dose vector (also referred to as final radiation dose vector) $d^F$. Determining the simulated radiation dose vector can include the treatment planning component 206 determining leaf movement and/or simulating radiation of the radiation beam. The treatment planning component 206 (or the optimization component 204) can then determine (or compute) the discrepancy between the optimization radiation dose vector $AX_3$ and the simulated radiation dose vector. The discrepancy can be computed as $\Delta = AX_3 - d^F$ by the optimization component 204 (or the treatment planning component 206).

The method 300 can include determining a fourth radiation beam profile by compensating for the determined radiation dose discrepancy (BLOCK 312). The optimization component 204 can employ an unconstrained formulation of the optimization problem defined by equation (3) and the constraints (3.a)-(3.f) that incorporates the radiation dose discrepancy $\Delta$. For instance, the optimization component 204 can determine the fourth radiation beam profile by solving the following optimization problem:

$$X_4 = \min_x \left( F_3(x) + \sum_{j \in J} \lambda_j \times g_j(Ax + \Delta) \right), \text{ subject to:} \quad (4)$$

$$\|x - X_3\|_2^2 \leq \epsilon, \text{ and} \quad (4.a)$$

$$x \geq 0. \quad (4.b)$$

The parameter $\lambda_j$ represent Lagrange multipliers and the function $g_j(Ax+\Delta)$ represent Lagrange functions for the constraints (3.a)-(3.f) with Ax replaced with $Ax+\Delta$ to compensate for the radiation dose discrepancy $\Delta$. Incorporating the radiation dose discrepancy $\Delta$ in the objective function $F_4(x) = F_3(x) + \sum_{j \in J} \lambda_j \times g_j(Ax+\Delta)$ of equation (4) allows for counter-balancing and compensating for such discrepancy. Given that the radiation dose discrepancy depends on the third radiation beam profile $X_3$, the hard constraint (4.a) allows for limiting the search space for the fourth radiation beam profile to a space in the vicinity of $X_3$.

The method 300 can include incorporating Dose Volume Constraints (DVCs) in the optimization process described above. For instance, the optimization component 204 can initially identify the voxels that are to receive low dose (or OARs' voxels) radiation and incorporate extra constraints, defined in inequalities (5) (or inequalities (5a) to (5c)) to represent the convex relaxation version of DVCs, into the optimization problem defined by equation (1). The optimization component 204 can solve the optimization problem defined by equation (1) with the additional DVCs incorporated as hard constraints or soft constraints. For a hard DVC that is required to be met, the optimization problems defined by equations (1) (3) can subsequently be solved with maximum dose constraints imposed on the low dose voxels. For a soft DVC that is desired to be met, but not required, the optimization problems defined by equations (1)-(3) can subsequently be solved where the violation of the DVC is allowed but discouraged and penalized in the objective function. For instance, a penalty term can be added to the objective function of equation (2). The DVCs can be defined as $$A_i^s x \leq d_s + Mb_i \text{ for all voxel } i \text{ in Structure } s: \quad (5)$$

$$\sum_i \frac{b_i}{n} \leq \frac{v_s}{100} \quad (5.b)$$

$$b_i \in [0, 1] \quad (5.c)$$

The terms $d_s$ and $v_s$ in (5.a) and (5.b) correspond to the dose volume constraint of $V(d_s \text{ Gy}) \leq v_s$ %, and M is a large positive number to hold the inequality (5.a) if $b_i$ is 1. For instance, M can be written as $M = (d_s^{max} - d_s)$.

In the objective function $F_2(x)$ of equation (2), a variety of dose based functions (e.g., instead of or other than the generalized equivalent uniform dose (gEUD) function) can be used, such as the minimum, maximum, mean values of doses in critical structures, (gEUD) functions, the rectified linear units (ReLUs) functions, or a combination thereof. The dose based functions represent damage to normal tissue (or corresponding voxels) as a function of radiation dose. ReLUs are functions of radiation dose (or radiation dose based functions) that have a value of zero below a certain threshold, but increase from zero above the threshold in a linear fashion, with a given slope. They are useful because they are simple to compute with and have desirable computational characteristics (e.g., they are convex functions). The ReLUs can be used as objective functions for individual anatomic structures (e.g., the right parotid gland), that introduce a threshold, below which further reductions in dose are not needed and have no effect on the optimizer. The slope of the ReLU controls how hard the optimizer will push this particular dose based (also referred to as dosimetric) characteristic. ReLUs can be introduced as a function of the mean dose of a structure, or of the maximum dose. We also introduce the use of sums of ReLUs that represent point doses to different regions of a structure. In this way, the overall sum of ReLUs can be introduced into the objective function, representing either the biological functional reserve of a structure, or possibly to represent the probability of a complication arising in different sub-units of a normal structure.

The optimization component 204 can provide the determined fourth radiation beam profile $X_4$ to the treatment planning component 206. The treatment planning component 206 can use the fourth radiation beam profile $X_4$ to generate a radiation plan, including leaf sequencing, to be applied to the patient. The treatment planning component 206 may also determine a radiation dose corresponding to the radiation beam profile $X_4$.

The method 300 for automated IMRT treatment planning, as described above, was used in an experiment of an automated IMRT treatment planning for SBRT Paraspinal cases using Eclipse as a TPS system. In this experiment, a physician contoured the organs of interest, and then a user defined the beam angles from which the patient should be irradiated. The user then runs ECHO as a plug-in from TPS and selects the structures that need to be part of the optimization. Once a radiation treatment plan is generated, typically after 1-3 hours, the user is notified via an email, and can evaluate the plan for treatment. Once the user runs the ECHO plug-in, the corresponding program performs the steps of method 300.

Figure 4:
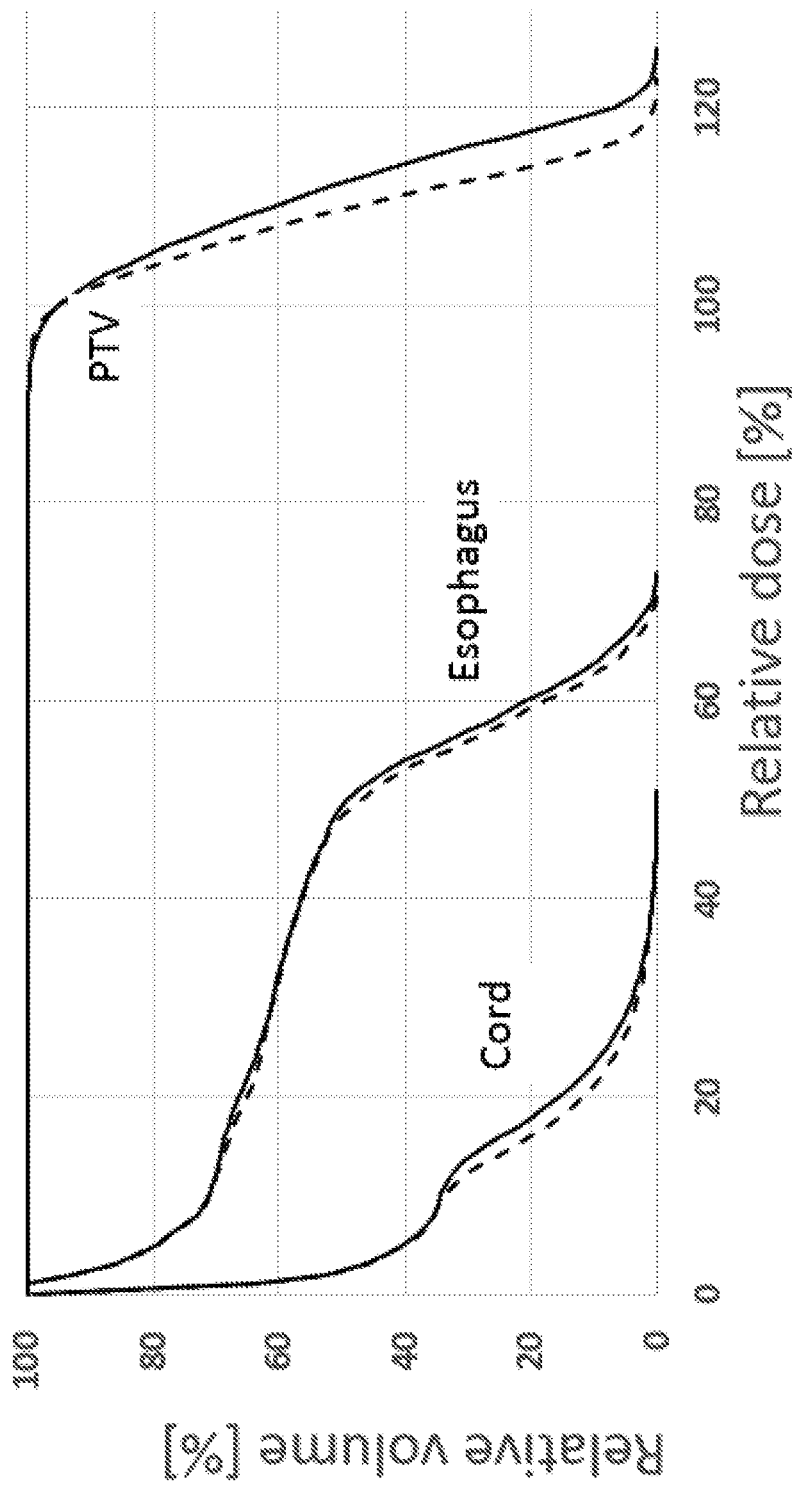
FIG. 4 shows experimental results illustrating the effect of a correction loop in the method of IMRT treatment planning.

Referring to FIG. 4, experimental results illustrating the effect of the correction loop (steps 310 and 312 of FIG. 3) in the method 300 are shown. The solid and dashed plots in FIG. 4 depict the dose-volume histograms (DVHs) of a radiation treatment plan before and after applying the correction loop, respectively. As can be seen in FIG. 4, the correction loop improves the PTV homogeneity and coverage as well as the cord and esophagus doses.

Figure 5:
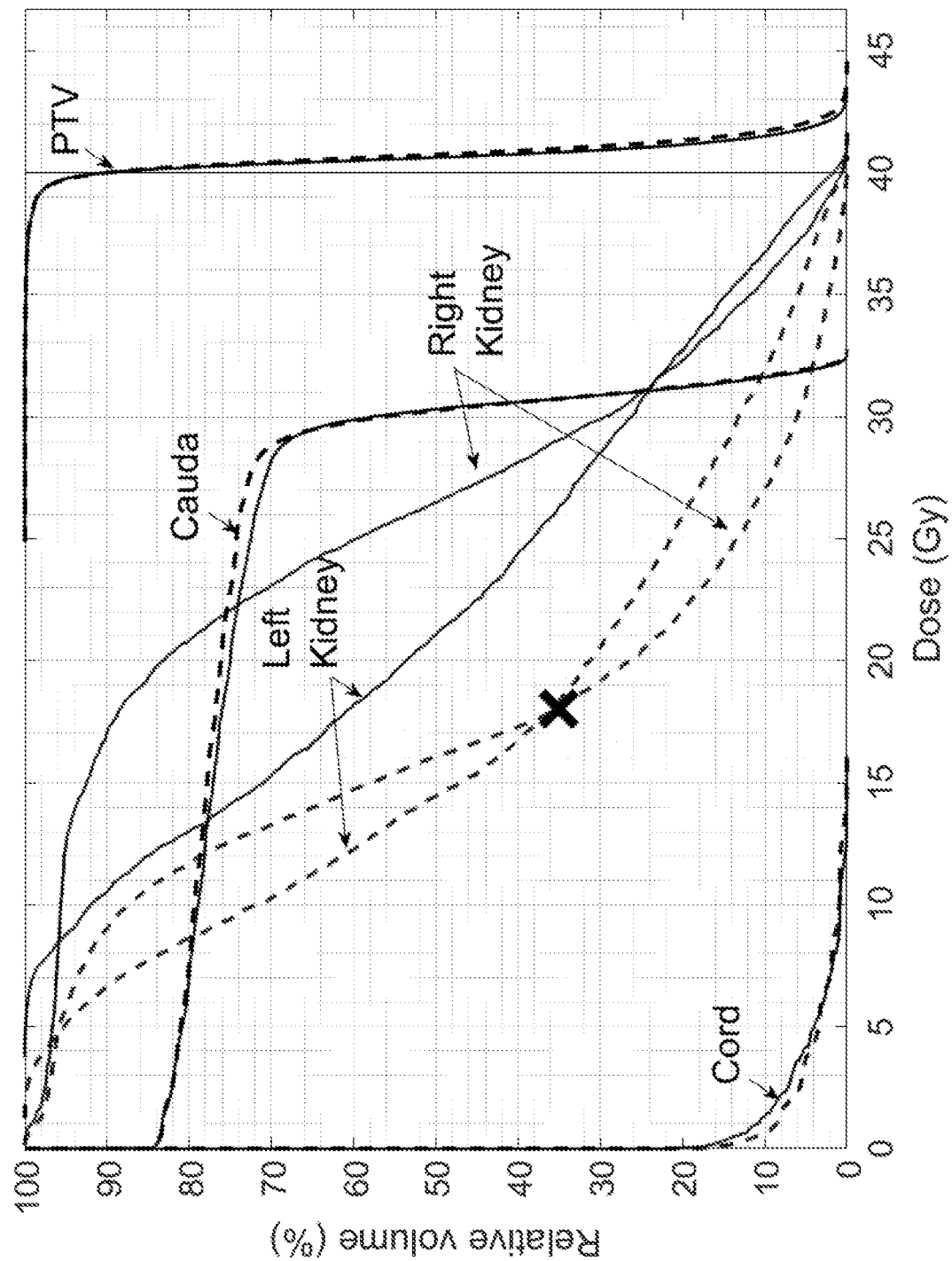
FIG. 5 shows experimental results illustrating the incorporation of hard dose volume constraints in the method of IMRT treatment planning.

Referring to FIG. 5 experimental results show the incorporation of hard DVCs, marked by 'x', on right and left kidneys on a paraspinal case in the method 300. The solid and dashed plots represent the results with and without incorporating DVCs. As can be seen, DVCs are satisfied at the cost of the PTV dose coverage and cauda dose. The computational time was increased by 20% for this case with respect to the algorithm without the DVC.

Figure 6:
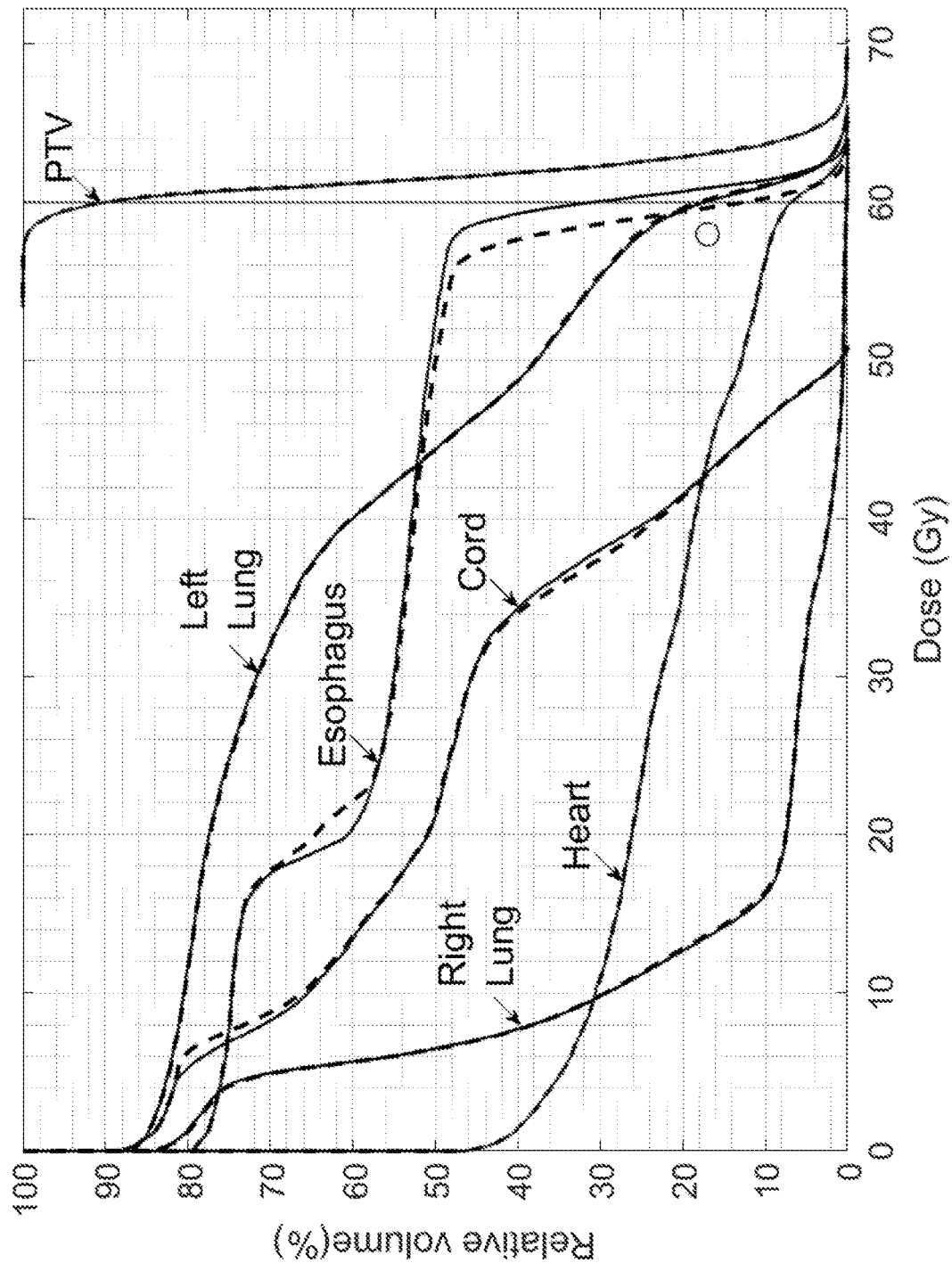
FIG. 6 shows experimental results illustrating the incorporation of soft dose volume constraints in the method of IMRT treatment planning.

Referring to FIG. 6 experimental results show the incorporation of a soft DVC, marked by 'o', on esophagus on a lung case in the method 300. The solid and dashed plots represent the results with and without incorporating DVCs. As can be seen, esophagus moves toward the desired direction without significant compromise of the PTV and OAR dose. The computational time was increased by 6% for this case.

Tables 1-a through 1-c below retrospectively compare the clinical plan against the automatically generated ECHO plan for 74 separate ECHO plans for 63 patients with different prescription and fractionation schemes and also with and without the previous radiation. Tables 1-a and 1-b represent the plans with three fractions and 27 Gy prescription while Table 1-c represents the single fraction plans with 24 Gy prescription. Patients in Table 1-a received radiation in the past and had different clinical criteria. The last column of the Tables 1-a through 1-c is indicative of the relative performance of the ECHO treatment plan and the clinical treatment plan (e.g., developed by a planner). The cells of the last column having a star represent the cases where the clinical treatment plan is superior to the ECHO treatment plan.

All ECHO plans met or exceeded the institution's clinical planning criteria and were more consistent and dosimetrically superior to the manually created plans. For example, for three fractions and 27 Gy prescription plans with patient receiving radiation in the past (Table 1-a), on average, ECHO improved PTV coverage (V95%) and CTV minimum dose by about 2% (p=0.002) and 19% (p=0.01) respectively, while it decreased cord and cauda maximum dose and esophagus D2.5cc(Gy) by about 16% (p=1), 4% (p=1) and 31% (p=0.9), respectively. ECHO slightly increased the cauda D5cc(Gy) by about 1% (p=1), but the ECHO plan was still within the institution acceptable range.

TABLE 1-a

| 27Gy Rx, three fractions, with previous Radiation, 24 plans | | ECHO | | Clinical | | Bonferroni Corrected (p) | Relative difference (Δ) |
|---|---|---|---|---|---|---|---|
| | | Average | SD | Average | SD | | |
| PTV | V95%(%) | 98.72 | 0.84 | 96.62 | 3.19 | 0.0024 | 2.15 |
| CTV | dMin(Gy) | 71.72 | 16.22 | 59.03 | 16.65 | 0.0126 | 19.40 |
| Cord | dMax(Gy) | 16.70 | 4.22 | 19.64 | 3.11 | 1 | 16.16 |
| | D0.35cc(Gy) | 12.80 | 6.26 | 14.08 | 5.59 | 1 | 9.52 |
| Cauda | dMax(Gy) | 24.24 | 0.85 | 25.28 | 0.68 | 1 | 4.19 |
| | D5cc(Gy) | 13.61 | 8.65 | 13.46 | 8.39 | 1 | 1.11 |
| Esophagus | D2.5cc(Gy) | 10.23 | 6.18 | 14.06 | 6.24 | 0.9375 | 31.55 |

TABLE 1-b

| 27Gy Rx, three fractions, 25 plans | | ECHO | | Clinical | | Bonferroni Corrected (p) | Relative difference (Δ) |
|---|---|---|---|---|---|---|---|
| | | Average | SD | Average | SD | | |
| PTV | V95%(%) | 99.11 | 1.01 | 98.72 | 1.44 | 0.3706 | 0.40 |
| CTV | dMin(Gy) | 84.48 | 9.36 | 81.15 | 10.6 | 1 | 4.02 |
| Cord | dMax(Gy) | 17.04 | 7.10 | 18.70 | 7.82 | 0.0467 | 9.31 |
| | D0.35cc(Gy) | 14.51 | 6.30 | 14.79 | 6.25 | 1 | 1.96 |
| Cauda | dMax(Gy) | 21.22 | 7.02 | 21.46 | 7.09 | 1 | 1.10 |
| | D5cc(Gy) | 9.57 | 10.08 | 8.84 | 9.33 | 0.5625 | 7.89 |
| Esophagus | D2.5cc(Gy) | 12.97 | 10.52 | 13.28 | 7.96 | 1 | 2.34 |

TABLE 1-c

| 24Gy Rx, single fraction, 25 plans | | ECHO | | Clinical | | Bonferroni Corrected (p) | Relative difference (Δ) |
|---|---|---|---|---|---|---|---|
| | | Average | SD | Average | SD | | |
| PTV | V95%(%) | 97.5644 | 1.97 | 96.5816 | 3.26 | 1 | 1.01 |
| CTV | dMin(Gy) | 70.41 | 12.62 | 69.72 | 11.87 | 1 | 0.98 |
| Cord | dMax(Gy) | 11.50 | 2.65 | 11.78 | 3.00 | 1 | 2.41 |
| | D0.35cc(Gy) | 9.04 | 2.21 | 9.04 | 2.37 | 1 | 0.00 |
| Cauda | dMax(Gy) | 12.69 | 7.22 | 13.86 | 7.85 | 0.375 | 8.82 |
| | D5cc(Gy) | 2.30 | 4.36 | 2.46 | 4.31 | 1 | 6.82 |
| Esophagus | D2.5cc(Gy) | 8.62 | 5.27 | 10.58 | 4.99 | 0.2988 | 20.35 |

D. Automated VMAT Planning

An extension of ECHO for VMAT can be achieved using similar steps as those of method 300 described with regard to FIG. 3. The ECHO-based VMAT radiation treatment planning technique can be viewed as including three phases with each phase associated with corresponding optimization problem(s). In the first phase, similar steps as BLOCKS 304 and 306 of FIG. 3 can be performed except that beamlets are replaced with a predefined set of potentially good apertures generated heuristically based on the projection of PTV and OARs into each angle's beam-eye-view. In the second phase, divergence between the neighboring apertures as well as the number of total apertures can be reduced to achieve or enhance delivery efficiency. The final phase can include a correction step (e.g., similar to steps as BLOCKS 310 and 312 of FIG. 3) to compensate for the inaccuracies resulting from approximation techniques in previous optimization phases. The problem of automated VMAT radiation treatment planning is solved hierarchically, using constrained optimization(s) at each of the phases described above.

Referring to FIG. 5, a flowchart illustrating a method 500 of volumetric modulated arc therapy (VMAT) treatment planning is shown, according to inventive concepts of this disclosure. The method 500 can include accessing patient specific data (BLOCK 502). The radiation modeling component 202 can break up the angular space into N equiangular intervals (num_intervals). The user or the radiation modeling component 202 can choose a number of initial apertures(init_apertures). Initial apertures can be chosen based on a heuristic. The radiation modeling component 202 can project the target volume plus a margin to form one aperture referred to as the beams-eye-view (BEV) aperture. The radiation modeling component 202 can subdivide the BEV aperture into the next 2 apertures. The radiation modeling component 202 can generate more apertures in the same way. Apertures are numbered (e.g., by the radiation modeling component 202) for each angle to allow optimization terms that link similar apertures from each angle. Once the apertures are generated, the radiation modeling component 202 can provide aperture information (e.g., corresponding angles, shapes, areas, or a combination thereof) to the optimization component 204 or store the apertures' information in a memory or database accessible by the optimization component 204.

The method 500 can include determining a first set of apertures (e.g., from a plurality of predefined apertures), and a corresponding first set of intensities by maximizing radiation to a PTV within anatomical sub-regions corresponding to normal tissues (or organs thereof), subject to a first set of constraints (BLOCK 504), and determining a second set of apertures and a corresponding second set of intensities minimizing radiation to normal tissue (e.g., by minimizing a dose based function) subject to a second set of constraints (BLOCK 506). The optimization component 204 can determine the first and second sets of apertures and the corresponding first and second sets of intensities by solving optimization problems similar to those defined by equations (1) and (2), respectively, with beamlet-intensity variables (vector variable x) replaced with aperture variables (e.g., apertures intensities and/or aperture geometry parameters), of the predefined set of radiation apertures.

The method 500 can include determining a third set of beam apertures and a corresponding third set of radiation intensities by reducing at least one of a number of beam apertures or dissimilarities between adjacent apertures associated with the second set of beam apertures (BLOCK 508). The optimization component 204 can determine third set of beam apertures and the corresponding third set of radiation intensities by solving an optimization problem that is formulated in a way to regularize the treatment plan to achieve or enhance delivery efficiency. Delivery efficiency can be enhanced by reducing the number of apertures (or enhancing sparsity) and/or enhancing similarities (e.g., in terms of shape and/or size) between adjacent or consecutive (along the rotational path of the radiation source) apertures. In analogy with BLOCK 308 of FIG. 3, the optimization component 204 can minimize the sum of two regularization factors (or minimize of these factors) subject to a defined allowed slippage on the results obtained from BLOCKS 504 and 506. The two regularization factors can include a first-norm-based shrinkage term and a sum of the distances that all leafs must be moved to convert one aperture into the next (adjacent) aperture. The first-norm-based shrinkage term can be equal to a first the sum of the aperture intensities (or apertures fluences) and is used to enhance the sparsity of the solution and reduce the number of apertures. The second regularization factor (sum of the distances that all leafs must be moved to convert one aperture into the other aperture) enforces relatively similar aperture shapes between angles where the 'earth mover's distance' between two apertures is used.

The method 500 can include identifying an arc-therapy radiation plan by computing a series of trajectories that link apertures from neighboring angular intervals or adjacent apertures (BLOCK 510). The optimization component 204 can include determining the discrepancy between the radiation dose associated with the arc-therapy plan from BLOCK 512 and the final radiation dose calculated by the treatment planning component 206. The optimization component 204 can include determining the final set of apertures and intensities by solving an optimization problem (e.g., unconstrained optimization problem) compensating for the determined radiation dose discrepancy (BLOCK 514). In analogy to Step 312 of FIG. 3, the optimization component 304 can use the radiation dose difference to adjust the apertures and their intensities to counter-balance the effect of the realistic arc paths. The optimization component can perform a further iteration of this step if desired.

For each of the sets of apertures discussed above and the corresponding sets of apertures intensities, each aperture in a given set is associated with a corresponding intensity in the corresponding intensity set.

E. Fast-ECHO for Radiotherapy Re-Planning

An extension of ECHO, referred to as fast-ECHO hereafter, to quickly adjust the radiation machine parameters based on the changes in the patient's anatomy can be achieved. Fast-ECHO can exploit the influence matrix calculation used for initial planning (BLOCK 202) after voxel re-assignment according to the anatomical changes. Fast-ECHO can include a single optimization problem to optimize the radiation machine parameters. In one implementation, the unconstrained optimization problem used for initial planning can be employed for re-planning.

In another implementation, the method can include solving a constrained optimization problem minimizing the weighted sum of the objective functions corresponding to tumor and OARs subject to a set of hard constraints. The objective functions, for example, could be the same functions used for the initial planning. Fast-ECHO could include a method to determine the objective functions' weights for each patient by learning from the database of previously ECHO-treated patients with similar planning protocols (i.e., same prescription, disease sites, and etc.).

Each method described in this disclosure can be carried out by computer code instructions stored on computer-readable medium. The computer code instructions, when executed by one or more processors of a computing device, can cause the computing device to perform that method.

While the disclosure has been particularly shown and described with reference to specific embodiments, it should be understood by those skilled in the art that various changes in form and detail may be made therein without departing from the spirit and scope of the invention described in this disclosure.

While this disclosure contains many specific embodiment details, these should not be construed as limitations on the scope of any inventions or of what may be claimed, but rather as descriptions of features specific to particular embodiments of particular inventions. Certain features described in this specification in the context of separate embodiments can also be implemented in combination in a single embodiment. Conversely, various features described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated in a single software product or packaged into multiple software products.

References to "or" may be construed as inclusive so that any terms described using "or" may indicate any of a single, more than one, and all of the described terms.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain embodiments, multitasking and parallel processing may be advantageous.

What is claimed is:

1. A method of intensity modulated radiation therapy (IMRT) treatment planning comprising:
   accessing, by one or more processors, patient specific data of a patient, the patient specific data including one or more parameters of an anatomical region of the patient, the anatomical region including a planning target volume (PTV) for which radiation to be applied and one or more anatomical sub-regions corresponding to normal tissues;
   determining, by the one or more processors using the patient specific data, a first radiation beam profile by maximizing radiation to the PTV subject to a first set of constraints;
   determining, by the one or more processors using the first radiation beam profile, a second radiation beam profile by minimizing one or more radiation dose based functions within the one or more anatomical sub-regions corresponding to the normal tissues subject to a second set of constraints;
   determining, by the one or more processors, a third radiation beam profile by smoothing the second radiation beam profile subject to a third set of constraints, smoothing the second radiation beam profile including reducing local variation of radiation intensity of the second radiation beam profile;
   determining, by the one or more processors, a radiation dose discrepancy between an optimization radiation dose vector associated with the third radiation beam profile and a simulated radiation dose vector determined based on the third radiation beam profile; and
   determining, by the one or more processors using the third radiation beam profile, a fourth radiation beam profile by reducing the determined radiation dose discrepancy.

2. The method of claim 1, wherein the second set of constraints includes the first set of constraints.

3. The method of claim 1, wherein the first set of constraints includes one or more dose volume constraints.

4. The method of claim 1, wherein the first radiation beam profile minimizes a discrepancy between a corresponding radiation dose vector and a target dose vector.

5. The method of claim 1, wherein the one or more radiation dose based functions include one or more generalized equivalent uniform dose based functions.

6. The method of claim 1, wherein the one or more radiation dose based functions include one or more rectified linear units (ReLUs) functions.

7. The method of claim 1, wherein determining the fourth radiation beam profile includes incorporating the radiation dose discrepancy in an unconstrained optimization problem using a Lagrange function.

8. The method of claim 1, wherein the patient specific data includes information indicative of at least one of a type, a location, a size or a shape of the PTV.

9. The method of claim 1, wherein the patient specific data includes information indicative of at least one of a type, a location, a size or a shape of an anatomical sub-region of the one or more anatomical sub-regions corresponding to normal tissues.

10. The method of claim 1, wherein the fourth radiation beam profile corresponds to a radiation treatment plan for applying to the patient.

11. A radiation treatment planning system for performing intensity modulated radiation therapy (IMRT) treatment planning, the radiation treatment planning system comprising:
   one or more processors; and
   a memory to store computer code instructions, the computer code instructions when executed cause the one or more processors to:
   access patient specific data of a patient, the patient specific data including one or more parameters of an anatomical region of the patient, the anatomical region including a planning target volume (PTV) for which radiation to be applied and one or more anatomical sub-regions corresponding to normal tissues;
   determine, using the patient specific data, a first radiation beam profile by maximizing radiation to the PTV subject to a first set of constraints;
   determine, using the first radiation beam profile, a second radiation beam profile by minimizing one or more radiation dose based functions within the one or more anatomical sub-regions corresponding to the normal tissues subject to a second set of constraints;

determine a third radiation beam profile by smoothing the second radiation beam profile subject to a third set of constraints, smoothing the second radiation beam profile including reducing local variation of radiation intensity of the second radiation beam profile;

determine a radiation dose discrepancy between an optimization radiation dose vector associated with the third radiation beam profile and a simulated radiation dose vector determined based on the third radiation beam profile; and determine, using the third radiation beam profile, a fourth radiation beam profile by reducing the determined radiation dose discrepancy.

12. The radiation treatment planning system of claim 11, wherein the second set of constraints includes the first set of constraints.

13. The radiation treatment planning system of claim 11, wherein the first set of constraints includes one or more dose volume constraints.

14. The radiation treatment planning system of claim 11, wherein the first radiation beam profile minimizes a discrepancy between a corresponding radiation dose vector and a target dose vector.

15. The radiation treatment planning system of claim 11, wherein the one or more radiation dose based functions include:
one or more generalized equivalent uniform dose based functions; or
one or more rectified linear units (ReLUs) functions.

16. The radiation treatment planning system of claim 11, wherein in determining the fourth radiation beam profile, the computer code instructions when executed cause the one or more processors to incorporate the radiation dose discrepancy in an unconstrained optimization problem using a Lagrange function.

17. The radiation treatment planning system of claim 11, wherein the patient specific data includes information indicative of at least one of a type, a location, a size or a shape of the PTV.

18. The radiation treatment planning system of claim 11, wherein the patient specific data includes information indicative of at least one of a type, a location, a size or a shape of an anatomical sub-region of the one or more anatomical sub-regions corresponding to normal tissues.

19. The radiation treatment planning system of claim 11, wherein the fourth radiation beam profile corresponds to a radiation treatment plan for applying to the patient.

20. A computer readable medium including computer code instructions stored thereon, the computer code instructions when executed cause one or more processors to:

access patient specific data of a patient, the patient specific data including one or more parameters of an anatomical region of the patient, the anatomical region including a planning target volume (PTV) for which radiation to be applied and one or more anatomical sub-regions corresponding to normal tissues;

determine, using the patient specific data, a first radiation beam profile by maximizing radiation to the PTV subject to a first set of constraints;

determine, using the first radiation beam profile, a second radiation beam profile by minimizing one or more radiation dose based functions within the one or more anatomical sub-regions corresponding to the normal tissues subject to a second set of constraints;

determine a third radiation beam profile by smoothing the second radiation beam profile subject to a third set of constraints, smoothing the second radiation beam profile including reducing local variation of radiation intensity of the second radiation beam profile;

determine a radiation dose discrepancy between an optimization radiation dose vector associated with the third radiation beam profile and a simulated radiation dose vector determined based on the third radiation beam profile; and determine, using the third radiation beam profile, a fourth radiation beam profile by reducing the determined radiation dose discrepancy.

\* \* \* \* \*